US012758588B2

(12) United States Patent
Soon-Shiong et al.

(10) Patent No.: US 12,758,588 B2
(45) Date of Patent: Oct. 13, 2026

(54) MESENCHYMAL STEM CELL DERIVED EXOSOMES AND METHODS

(71) Applicant: NantBio, Inc., Culver City, CA (US)

(72) Inventors: Patrick Soon-Shiong, Culver City, CA (US); Francesco Curcio, Culver City, CA (US); Kayvan Niazi, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 18/415,194

(22) Filed: Jan. 17, 2024

(65) Prior Publication Data

US 2024/0148793 A1 May 9, 2024

Related U.S. Application Data

(62) Division of application No. 17/284,969, filed as application No. PCT/US2019/056804 on Oct. 17, 2019, now Pat. No. 12,263,189.

(60) Provisional application No. 62/747,605, filed on Oct. 18, 2018.

(51) Int. Cl.
*A61K 35/28* (2015.01)
*A61K 45/06* (2006.01)

(52) U.S. Cl.
CPC .............. *A61K 35/28* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 12,263,189 | B2 | 4/2025 | Soon-Shiong et al. |
| 2015/0093363 | A1 | 4/2015 | Ekstrom et al. |
| 2016/0317583 | A1 | 11/2016 | Weiss et al. |
| 2021/0353684 | A1 | 11/2021 | Soon-Shiong et al. |

FOREIGN PATENT DOCUMENTS

| | | | |
|---|---|---|---|
| CA | 2743211 | * | 5/2017 |
| KR | 101865040 | B1 | 6/2018 |
| WO | 2015142061 | A1 | 9/2015 |
| WO | 2018/071677 | A1 | 4/2018 |
| WO | 2018/071681 | A1 | 4/2018 |
| WO | 2018/080990 | A1 | 5/2018 |
| WO | 2018/183194 | A1 | 10/2018 |
| WO | 2020/081859 | A1 | 4/2020 |

OTHER PUBLICATIONS

First Office Action received for the Chinese Patent Application Serial No. 201980068667.6 dated Mar. 30, 2023, 32 pages. (Including English Translation).

Teng et al., "Suppression of inflammation by tumor-derived exosomes: a kind of natural liposome packaged with multifunctional proteins", Journal of Liposome Research, vol. 22, No. 4, 2012, pp. 346-352.

Domenis et al., "Toll-like Receptor-4 Activation Boosts the Immunosuppressive Properties of Tumor Cells-derived Exosomes", Scientific Reports, vol. 9, Article No. 8457, Jun. 11, 2019, pp. 1-14.

Crisostomo et al., "Human mesenchymal stem cells stimulated by TNF-alpha, LPS, or hypoxia produce growth factors by an NF kappa B- but not JNK-dependent mechanism", American Journal of Physiology—Cell Physiology, vol. 294, No. 3, 2008, pp. C675-C682.

Second Office Action received for the Chinese Patent Application Serial No. 201980068667.6 dated Nov. 22, 2023, 28 pages. (Including English Translation).

Third Office Action received for the Chinese Patent Application Serial No. 201980068667.6 dated Feb. 3, 2024, 23 pages. (Including English Translation).

European Extended Search Report received for the European Application No. 19873618.3 dated Jun. 22, 2022, 08 pages.

Prasanna et al., "Pro-Inflammatory Cytokines, IFN and TNF, Influence Immune Properties of Human Bone Marrow and Wharton Jelly Mesenchymal Stem Cells Differentially", PLOS ONE, vol. 5, No. 2, Feb. 2, 2010 (Feb. 2, 2010), p. e9016.

Crisostomo et al., Human mesenchymal stem cells stimulated by TNF-α, LPS, or hypoxia produce growth factors by an NFκB- but not JNK-dependent mechanism, American Journal of Physiology—Cell Physiology, vol. 294, Issue 3, Mar. 2008, pp. c675-c682.

Peterson et al., "Integrated systems for exosome investigation", Methods, 2015, pp. 1-15 (Cited from Specification).

International Search Report and Written Opinion received for International PCT Application Serial No. PCT/US2019/056804 dated Feb. 7, 2020, 10 pages.

Domenis et al., "Pro inflammatory stimuli enhancethe immunosuppressive functionsof adipose mesenchymal stem cellsderivedexosomes", Scientific Reports, 2018, vol. 8, No. 13325, pp. 1-11.

International Preliminary Report on Patentability Chapter I received for International PCT Application Serial No. PCT/US2019/056804 dated Apr. 29, 2021, 8 pages.

Examination Report received for European Application No. 19873618.3 dated Mar. 14, 2025, 4 pages.

(Continued)

*Primary Examiner* — Michael V Meller
(74) *Attorney, Agent, or Firm* — Umberg Zipser LLP; Martin Fessenmaier; Priti Phukan

(57) ABSTRACT

Compositions and methods are presented that include exosomes from stem cells and/or tumor cells that were previously exposed to an inflammatory stimulus. Advantageously, such exosomes exhibit anti-inflammatory and analgesic effect when administered to an individual. Therefore, a preferred use of such exosomes will reduce the need for opioid analgesics, and reduce pain and inflammation.

7 Claims, 12 Drawing Sheets

(56) References Cited

OTHER PUBLICATIONS

Tan et al., “Role of Adipose-derived Stem Cells in Fat Grafting and Reconstructive Surgery”, J Cutan Aesthet Surgm, Jul.-Sep. 2016; 9 (3), 152-156 Pages.

* cited by examiner

G

F

MESENCHYMAL STEM CELL DERIVED EXOSOMES AND METHODS

CROSS-REFERENCE TO RELATED APPLICATIONS

This application is a divisional application of U.S. patent application Ser. No. 17/284,969, filed Apr. 13, 2021, which is a 35 U.S.C. § 371 U.S. National Stage Entry of International Application No.: PCT/US2019/056804, filed Oct. 17, 2019, which claims priority to US Provisional Patent application with the Ser. No. 62/747,605, filed Oct. 18, 2018. The contents of each of these applications are herein incorporated by reference in its entirety.

FIELD OF THE INVENTION

The present disclosure relates to compositions and methods of use of exosomes, especially of exosomes derived from cells previously stimulated with inflammatory stimuli in the treatment of pain and/or inflammation.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Control of pain, and particularly post-operative pain and pain associated with (chronic) inflammation can be controlled in a variety of manners. Most commonly, pain can be treated with non-steroidal anti-inflammatory drugs (NSAIDs), various drugs that reduce central nervous sensitization, and opioid-type analgesics. NSAIDs are typically well tolerated, even at relatively high dosages, but are often not sufficient for pain control. On the other hand, opioid analgesics are often highly effective in reduction of pain, but are often associated with tolerance and risk of dependency.

For example, most NSAIDs act by inhibiting COX enzymes and reduce the formation of prostaglandins. While non-selective inhibition of COX produces a significant anti-hyperalgesic effect and emphasizes the importance of prostaglandins in inflammatory hyperalgesia, clinical use is often limited by serious gastrointestinal side effects. Recently, selective COX-2 inhibitors were introduced to reduce these adverse effects. However, selective COX-2 inhibitors were accompanied by significant cardiac risk. To circumvent difficulties associated with COX, the actions of prostaglandins can be substantially reduced by selective receptor blockade. The most promising approach uses antagonists of the EP receptor subfamily, which are present on sensory neurons and are activated by PGE2. In still further known methods, NSAIDs may be modified to release nitric oxide to provide improved anti-nociceptive and anti-inflammatory effects. However, such treatments are mostly experimental.

Opiates are produced by immune cells, and opioid receptors are present in peripheral tissues. Notably, expression of μ, δ and κ receptors increases in primary afferent neurons during inflammation and selective agonists block spontaneous firing of fibers which innervate inflamed skin. Moreover, opioid agonists developed for peripheral use often show anti-nociceptive activity in inflammatory conditions such as experimental arthritis. Potentially, peripherally acting opioid compounds may provide pain relief in inflammatory conditions by systemic or even topical application. However, use of opioids has a high risk of dependency or addiction as evidenced by the recent opioid crisis.

In yet further known methods of treating pain, cannabinoids can be administered to reduce or inhibit peripheral sensitization using two types of cannabinoid receptors, CB1 and CB2. The former is expressed on central and peripheral neurons as well as on non-neuronal cells, whereas the latter is of non-neuronal origin and is present on immune cells. Activation of the CB1 receptor is negatively coupled to adenylate cyclase and blocks excitability and activation of primary afferents. Activation of the CB2 receptor may produce anti-nociceptive effects via inhibition of immune cell functions. However, pain management using cannabinoids is largely experimental and may not be suitable for severe pain.

Thus, even though various analgesics are known in the art, all or almost all of them suffer from various disadvantages. Consequently, there is a need to provide improved compositions and methods that provide effective pain control without high risk of adverse events.

SUMMARY OF THE INVENTION

Various compositions and methods that employ exosomes as therapeutic agents are disclosed herein, where the exosomes are derived from cells that were previously stimulated with an inflammatory agent. Advantageously, such exosomes have been demonstrated to have anti-inflammatory and/or analgesic properties.

In one aspect, a method of reducing the need for opioid analgesia in an individual is disclosed herein. Preferred methods include a step of administering to the individual: (1) a composition that includes exosomes from stem cells and/or tumor cells that were previously exposed to one or more inflammatory stimulus; and/or (2) a composition that includes cells (e.g., mesenchymal stem cells) that secrete an anti-inflammatory cytokine (e.g., tumor growth factor β). For example, the individual may be diagnosed with an inflammatory condition or cancer, or may have undergone surgery (e.g., joint replacement surgery).

In some embodiments, the exosomes are derived from (e.g., adipose) mesenchymal stem cells, while in other embodiments the exosomes are derived from tumor cells. Preferably, but not necessarily, the exosomes are from the stem cells or the tumor cells of the same individual. With respect to the inflammatory stimulus it is contemplated that the stimulus IFNγ (interferon gamma), TNFα (tumor necrosis factor alpha), a TLR ligand, a NOD ligand, and/or a STING (Stimulator of Interferon Genes) activator. Typically, the stem cells or the tumor cells will be exposed to the inflammatory stimulus in an amount that increases expression of IDO (indoleamine-2,3-dioxygenase) or $PGE_2$ (prostaglandin E2) in the stem cells or the tumor cells, and/or in an amount that increases IL-6, IL-8, IL10, or CCL-2 in the stem cells or the tumor cells. Where desired, the composition is formulated for injection and/or will comprise at least $10^7$ exosomes, or at least $10^8$, or at least $10^9$ exosomes per dosage unit.

In another aspect, methods of treating an inflammatory conditions and associated pain in an individual are disclosed herein. Such methods will comprise a step of administering to the individual a composition that comprises exosomes from stem cells and/or tumor cells that were previously exposed to one or more inflammatory stimulus.

Most typically, the individual is diagnosed with a chronic inflammatory condition, or has undergone treatment for cancer or joint replacement surgery. As noted before, it is preferred that the exosomes are from mesenchymal stem cells, and most typically from the stem cells of the same individual. Suitable inflammatory stimuli include IFNγ (interferon gamma), TNFα (tumor necrosis factor alpha), TLR ligands, NOD ligands, and/or STING (Stimulator of Interferon Genes) activators. Moreover, it is contemplated that the stem cells or the tumor cells are exposed to the inflammatory stimulus in an amount that increases expression of IDO (indoleamine-2,3-dioxygenase) or $PGE_2$ (prostaglandin E2) in the stem cells or the tumor cells, and/or that the stem cells or the tumor cells are exposed to the inflammatory stimulus in an amount that increases IL-6, IL-8, IL10, or CCL-2 in the stem cells or the tumor cells.

In a further aspect, methods of manufacturing a pharmaceutical composition are disclosed herein. Such method will include a step of exposing stem cells and/or tumor cells of an individual ex vivo in a culture medium to an inflammatory stimulus. In a further step, exosomes are harvested from the culture medium, and in yet another step, the harvested exosomes are formulated into a pharmaceutical composition suitable for injection or infusion.

For example, suitable stem cells include mesenchymal stem cells (e.g., adipose mesenchymal stem cells), while contemplated inflammatory stimuli include IFNγ (interferon gamma), TNFα (tumor necrosis factor alpha), a TLR ligand, a NOD ligand, and/or a STING (Stimulator of Interferon Genes) activator. Most typically, the stem cells or the tumor cells are exposed to the inflammatory stimulus in an amount that increases expression of IDO (indoleamine-2,3-dioxygenase) or $PGE_2$ (prostaglandin E2) in the stem cells or the tumor cells, and/or in an amount that increases IL-6, IL-8, IL10, or CCL-2 in the stem cells or the tumor cells. In further contemplated embodiments, the stem cells or the tumor cells are exposed to the inflammatory stimulus for at least 24 hours, or at least 36 hours, or at least 48 hours.

In some embodiments, the exosomes are harvested using a step of ultracentrifugation or a step of polymer precipitation, while in other embodiments the exosomes are harvested using a step of affinity separation using an antibody or fragment thereof. Preferred pharmaceutical composition comprises at least $10^7$ exosomes, or at least $10^8$, or at least $10^9$ exosomes per dosage unit. Where desired, an anti-inflammatory agent and/or an analgesic drug may be included into the pharmaceutical composition.

Therefore, pharmaceutical compositions comprising a plurality of stimulated stem cell- or stimulated tumor cell-derived exosomes are disclosed herein, wherein the composition is formulated for injection or infusion. For example, the stimulated stem cell-derived exosomes are from mesenchymal stem cells, and the exosomes may be autologous exosomes with respect to an individual receiving the exosomes. With respect to the cell stimulation and the formulation, the same considerations as noted above apply. Suitable compositions may further include an NSAID and/or an anti-inflammatory cytokine or chemokine.

Exosomes from stem cells and/or tumor cells that were previously exposed to one or more inflammatory stimulus for use in medicine are also disclosed herein. While not limiting the present disclosure, it is preferred that the exosomes have an average particle size of between about 70 nm to about 130 nm, that the exosomes are from mesenchymal stem cells, and/or that the exosomes are from tumor cells. Most typically, the exosomes are from stem cells or tumor cells of the same individual (autologous exosomes). With respect to the cell stimulation and the formulation, the same considerations as noted above apply. In addition, it is contemplated that preferred uses in medicine include the treatment of an inflammatory condition and/or the treatment of pain.

Various objects, features, aspects, and advantages will become more apparent from the following detailed description of preferred embodiments, along with the accompanying drawing in which like numerals represent like components.

DETAILED DESCRIPTION

Figure 1:
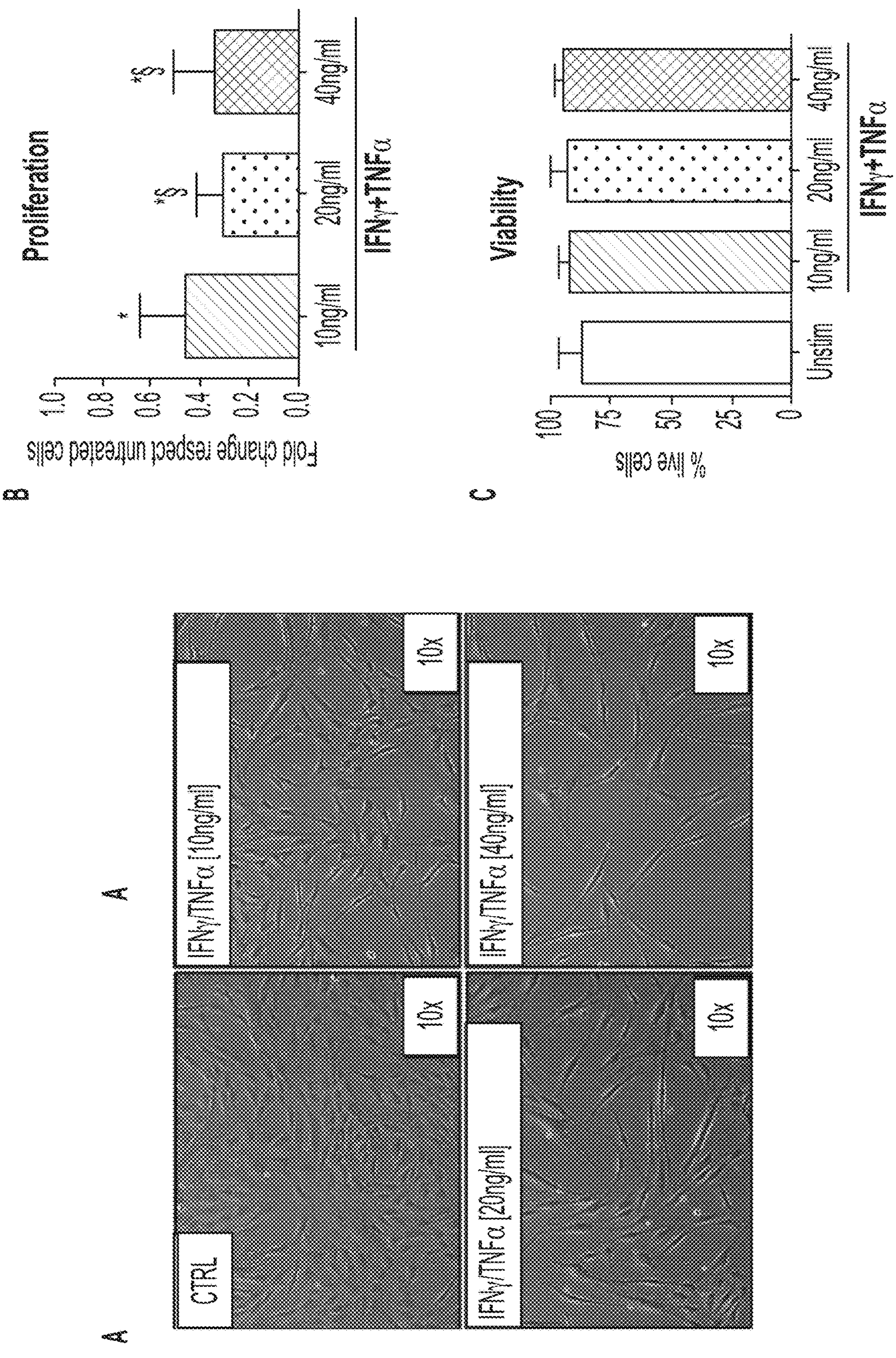
FIG. 1 depicts results illustrating that stimulation with IFNγ/TNFα mixture induces morphological changes and inhibits proliferation of AMSCs. (A) Representative phase contrast images (10× magnification) of AMSCs incubated with IFNγ/TNFα at concentration of 10, 20 and 40 ng/ml for 48 hours. (B-C) Cell proliferation and viability were determined by trypan blue exclusion assay. Columns, mean; bars, SD*significant difference from unstimulated cells; § significant difference from treatment with IFNγ/TNFα at concentration of 10 ng/ml, $P<0.05$.

Pain, and especially pain associated with surgery and/or inflammatory conditions can be treated by administration of exosomes having pronounced analgesic and anti-inflammatory activity that reduce the need for opioid analgesics and that also downregulate inflammation. Especially suitable exosomes include those derived from stem cells and/or tumor cells that were previously exposed to one or more inflammatory stimuli. Further contemplated treatments may also include administration of cells (e.g., stem cells) that secrete anti-inflammatory cytokines, such as TGF-β, where such cells were also previously exposed to one or more inflammatory stimuli. Likewise, it should be appreciated that contemplated compositions and methods may also include only parts of exosomes, and particularly regulatory proteins, RNA, and/or miRNA isolated from exosomes.

For example, pain associated with joint replacement such as knee or hip replacement can be treated by injection of a pharmaceutical composition into the repair site (e.g., in bursa of the knee), typical using at least $10^7$ (e.g., at least $10^8$ or at least $10^9$) exosomes per administration. Most preferably, the exosomes will be derived from adipose mesenchymal stem cells of the same patient that receives the exosomes to so reduce the risk of an immune response against components of the exosomes. In general, the administration of exosomes will be via injection, typically into or proximal to the site of pain and inflammation, at least one, and more typically at least twice (e.g., over a period of 2-6 weeks). While not limiting the present disclosure, the analgesic effect of the exosomes contemplated herein will be accomplished via at least two distinct modes of action: exosomes may directly or indirectly inhibit or reduce pain-associated effectors and down-regulate inflammation via anti-inflammatory signals.

Of course, it should be noted that various pain conditions other than joint replacement are also deemed suitable for use herein and will generally include all pain conditions associated with inflammation, tissue trauma, and tumors. For example, pain conditions that are associated with inflammation include autoimmune disorders, pain associated with chronic inflammation, while pain associated with tissue trauma may be due to accidental injury, surgery, etc. Likewise, pain associated with many tumors is typically not dependent on the particular tumor type. In at least some embodiments, particularly preferred cells are stem cells such as mesenchymal stem cells. However, other types of stem cells such as epidermal or endodermal stem cells are also deemed suitable for use herein. Moreover, it should be noted that suitable stem cells may also include pluripotent and totipotent stem cells (i.e., developmentally more 'upstream'), and progenitor cells of specific tissues (i.e., developmentally more 'downstream'). In still further embodiments, suitable cells need not be limited to stem cell or progenitor cells, but may also include tumor cells, various leukocytes, and thrombocytes. Therefore, suitable stem cells may be derived from bone marrow, adipose tissue, cord blood, etc.

Regardless of the particular cell type used to generate the exosomes, it is preferred that the cells are autologous with respect to the individual receiving the exosomes. Alternatively, the cells may also be from a different individual. In that case, it is generally preferred that there is HLA compatibility between the cell and the individual receiving the exosomes for at least four HLA subtypes (e.g., HLA-A, HLA-B, HLA-C, HLA-DR, HLA-DQ, HLA-DP) to a depth of at least two, and more typically at least four digits.

Not all exosomes from all cells will exhibit analgesic and/or anti-inflammatory effect, but that exosomes with analgesic and/or anti-inflammatory effect will generally be derived from cells previously subjected to a pro-inflammatory or other cell stress stimulus. Notably, various inflammatory conditions will promote the generation of exosomes having pronounced anti-inflammatory activity, which can be used as component in various treatments and treatment compositions. For example, exosomes prepared as described herein will inhibit or reduce CD4+ and CD8+ T cell proliferation, will modulate macrophage polarization, and/or favor Treg development. Moreover, it was observed that exosomes may also present NKG2D ligands and as such may act as soluble NKG2D ligands leading to so lead to NK cell inactivation.

For example, to generate exosomes with analgesic and/or anti-inflammatory effect, cells will be cultivated ex vivo in the presence of an inflammatory (or otherwise stress) stimulus, most typically for a period of at least 6 hours, or at least 12 hours, or at least 24 hours, or at least 36 hours, or at least 48 hours. Depending on the type of cells, cell culture can be performed under normoxic or hypoxic conditions. For example, stem cells and tumor cells may be cultivated at about 21 vol % $O_2$, or between 15-20 vol %, or between 10-15 vol %, or between 5-10 vol %, or between 1-5 vol %. Most typically, cell cultivation will be at 35-39° C., and in some cases between 37-42° C. The skilled artisan will readily determine the appropriate cell culture medium for the selected cells. In certain non-limiting embodiments, the exosomes can then be harvested by ultracentrifugation, for example centrifugation at a force greater than 10 g (e.g., greater than 50 g, greater than 100 g, greater than 500 g, greater than 1000 g, or greater than 5000 g) for at least 15 min. (e.g., at least 30 min., at least 45 min., at least 1 hr., at least 5 hrs., at least 10 hrs., or at least 12 hrs.). Additionally or alternatively, the exosomes can be harvested from culture medium or centrifuged precipitate by polymer precipitation, as described by (e.g.) Peterson et al. (2015) *Methods* 87:31-45.

With respect to the inflammatory stimulus it is contemplated that the stimulus is provided to the cells in culture in continuous (e.g., via pump) or intermittent (e.g., via media replacement) manner using concentrations that will trigger an appropriate response (e.g., induction of gene expression, secretion of soluble factors or presentation of receptors, activation of cell signaling, etc.). For example, contemplated inflammatory stimuli include pro-inflammatory cytokines such as IFNγ (interferon gamma), TNFα (tumor necrosis factor alpha), one or more TLR ligands, one or more NOD ligands, and/or one or more STING (Stimulator of Interferon Genes) activators. Concentrations of these stimuli to exert biological effects are generally well known in the art, and all such concentrations are deemed suitable for use herein. In yet other embodiments, the (e.g., stem or tumor) cells will be exposed to the inflammatory stimulus in an amount that increases expression of IDO (indoleamine-2,3-dioxygenase) or $PGE_2$ (prostaglandin E2) in the so exposed cells, and/or in an amount that increases IL-6, IL-8, IL10, and/or CCL-2 in the cells. Thus, especially suitable cells and stimuli are chosen such that the pro-inflammatory stimulus will trigger an anti-inflammatory cell response.

Still further contemplated stimulants include polymannuronic acid and other immune stimulating (hetero)polysaccharides commonly found in bacteria, algae, and fungi such as polysaccharide A, protein-bound polysaccharides PSK or PSP, lipopolysaccharide (LPS), hyaluronic acid, and various β-(1,3)-glucans.

After appropriate time of cell culture, exosomes can then be collected from the culture medium using all manners known in the art. For example, exosomes may be collected by first removing the cells from the medium, and then by ultracentrifugation of the medium to pellet the exosomes. Alternatively, exosomes may also be isolated using polymeric precipitation (e.g., using EXOQUICK™ from SBI Biosystems) or precipitation with Annexin V, or using various affinity reagents (e.g., antibodies against exosome-specific markers CD9, CD81, and Hsp70). Regardless of the manner of isolation, it is generally preferred that the isolated exosomes be further purified (e.g., using dialysis or membrane filtration) before the exosomes are formulated for injection. Suitable pharmaceutical compositions will generally comprise one or more different types of exosomes (derived from one or more different types of treated cells) in an amount of at least $10^6$, or at least $10^7$, or at least $10^8$, or at least $10^9$ exosomes per dosage unit (e.g., 1-5 mL). As will be readily appreciated, suitable liquid carriers for injection of infusion include isotonic solutions, and especially isotonic saline, dextrose, and/or lactate solutions. Moreover, contemplated compositions may further include one or more known analgesic and/or anti-inflammatory agent, typically in quantities as commonly prescribed and published in the respective prescribing information.

Alternatively, isolated exosomes may also be further processed to isolate or identify one or more mediator molecules in the exosomes that exert the anti-inflammatory and/or analgesic effect, and especially contemplated mediators include mRNA, miRNA, and various protein components (which may or may not be membrane anchored). In such case, the mediators will be characterized and used alone or in combination with other analgesic and/or anti-inflammatory agents for formulation into a pharmaceutical composition. Additionally, it was observed that exosomes from stimulated cancer cells (e.g., SW-480) had significant quantities of selected integrins, and particularly integrin-α5 and integrin-β5. As these integrins were reported to be relevant to the homing of cancer derived exosomes in metastatic target tissues, blockers (e.g., antibodies, fragments thereof, or other high-affinity binders) of these molecules can be used in a pharmaceutical composition to reduce homing of exosomes to distant sites.

Consequently, exosomes from stimulated cells can be particularly useful in the treatment of an individual in need thereof, particularly where the individual has an inflammatory condition (especially has pain associated with an inflammatory condition) and/or suffers from pain. As such, contemplated methods and compositions will reduce the need for opioid analgesics and thus greatly reduce the risk for habituation and dependence. Thus, contemplated compositions can be used to treat inflammation and reduce pain associated with inflammation.

Examples

Adipose mesenchymal stem cells isolation and culture: Adipose mesenchymal stem cells (AMSCs) were isolated from adipose tissue obtained by lipoaspirates. A total number of six lipoaspirate samples were collected after informed written consent of donors. Lipoaspirates were enzymatically dissociated using a 0.05% collagenase II solution for 20 minutes at 37° C. (Worthington) and, after neutralization of the enzyme, were centrifuged at 500×g for 5 minutes and filtered through a 70 m nylon mesh (Merck Millipore). Cells were seeded in minimum essential medium-α (MEM-α) supplemented with 10% FBS (Gibco), penicillin/streptomycin solution (10 mL/L), alanine/glutamine solution (2 mM), human epidermal growth factor (10 ng/ml), insulin solution (10 μg/ml), 2-phospho-L-ascorbic acid, trisodium salt (100 μM) and dexamethasone (0.01 μM) (all from Sigma-Aldrich). Culture were kept at 37° C., 5% CO2 and 95% humidity and cells were characterized by flow cytometry using MSCs positive markers (CD29, CD73, CD90 and CD105) and hematopoietic negative markers (CD34 and CD45). Cells were used for experiment between passage 2 and 5.

Activation of adipose mesenchymal stem cells with IFNγ and TNFα: To activate AMSCs with inflammatory factors, cells were seeded at density of 15,000 cells/$cm^2$ and after 24 hours supernatant was replaced with fresh culture medium supplemented with 5% certified exosomes-free serum (Gibco) with recombinant human IFNγ and TNFα (Prepotech) at different concentrations (10, 20 and 40 ng/ml). The concentration 10 ng/ml corresponds to 200 U/ml. After 48 hours, AMSCs were harvested and cell proliferation/viability was determined by trypan blue exclusion assay. For flow cytometry analysis, AMSCs were fixed and permeabilized with intracellular Fix/Perm solution (eBiosciences), incubated with FITC-conjugated indoleamine-pyrrole 2,3-dioxygenase (IDO) antibody (eBiosciences) for 15 min and then washed twice with PBS. Flow cytometry was carried out on the FACSCalibur (Becton Dickson) and data analyzed using Flowing software. Supernatants were also harvested, centrifuged for 10 minutes at 14,000×g and stored at −80° C. for exosomes isolation or cytokines detection. The concentration of IL-6, IL-10, IL-8 and CCL-2 was determined with a magnetic beads-based multiplex assay (Bio-plex Assay, Bio-Rad Laboratories), while prostaglandin E2 release (PGE2) was quantified with an enzyme-linked immunosorbent assay (ELISA) kit (Invitrogen).

Exosomal RNA isolation, library preparation/sequencing and RT-PCR: To preserve small RNAs, total RNA was extracted from $5\times10^9$ AMSCs-derived exosomes, using mirVana PARIS Kit (Life Technologies), adding cel-miR39 spike-in as exogenous control (ThermoFisher Scientific). Extracted RNA quality and quantity was evaluated by NanoDrop™ 1000 Spectrophotometer (ThermoFisher Scientific) and was stored at −80° C. until use.

For miRNA profiling analysis, a pool of AMSCs-derived exosomes obtained in five different purification was examined. 'TruSeq SmallRNA Sample Prep kit' (Illumina) has been used for library preparation following the manufacturer's instructions. Both RNA samples and final libraries were quantified by using the Qubit 2.0 Fluorometer (Invitrogen) and quality tested by Agilent 2100 Bioanalyzer RNA Nano assay (Agilent technologies). Libraries were then processed with Illumina cBot for cluster generation on the flowcell, following the manufacturer's instructions and sequenced on single-end mode on NextSeq 500 (Illumina, San Diego, CA). The CASAVA 1.8.2 version of the Illumina pipeline was used to processed raw data for both format conversion and de-multiplexing.

The relative concentrations of miRNAs involved in regulation of macrophages M1 (has-miR-21-5p, has-miR-127-3p and has-miR-155-5p) and M2 (has-miR-34a-5p, has-miR124-3p, has-miR135b-5p and hsa-miR146a-5p) polarization were assessed using TaqMan® Advanced miRNA Assays (ThermoFisher Scientific), according to manufacturer's instructions, except for cDNA templates that were diluted 1:2 instead of recommended 1:10.

Real-time reaction was performed on the Applied Biosystems QuantStudio 3 System. MiRNA relative concentrations were normalized using relative standard curve method obtained by serial dilutions of cel-miR39 (1 nM-100 fM).

Monocytes isolation and differentiation into M1 macrophages: Human peripheral blood mononuclear cells (PBMCs) were isolated from EDTA-uncoagulated blood of blood donors by Ficoll gradient centrifugation (Millipore). Monocytes were separated from PBMCs by negative selection using a human CD14+ cell enrichment kit (StemCell Technologies) according to the manufacturer's instructions and resuspended in RPMI medium supplemented with 10% heat inactivated fetal bovine serum (FBS), 1% glutamine, 1% pyruvate, 1% non-essential amino acid, 1% penicillin/streptomycin, 1% Hepes (all from Euroclone). To remove the exosomal fraction present in FBS, serum was ultracentrifuged for 4 hours at 100,000×g. Purity of monocytes was over 95% as judged by staining with anti-CD14 (eBiosciences) (data not shown).

For macrophages differentiation, CD14+ monocytes were seeded in multiwell plates at $5\times10^5/cm^2$ in complete RPMI medium supplemented with 100 ng/ml granulocyte macrophage-colony stimulating factor (GM-CSF, Peprotech) in presence of $8\times10^8$ AMSC-derived exosomes; medium was changed completely every 3 days. On day 9, macrophages was harvested with TrypLE™ express detachment solution (Gibco) and characterized by flow cytometry for the expression of M1 and M2 macrophages markers using CD80, CD206 and CD163 antibodies (eBiosciences). Macrophages were also lysed in RIPA buffer and expression of IRAK1, Notch1 and SIRPb1 was analysed by immunoblotting. Anti-IRAK1 (1:1000, Cell Signalling), anti-β-actin (1:5000, Cell Signalling), anti-Notch1 (1:500, Cell signalling) and anti-Sirp-β1 (1:200, Santa Cruz Biotecnologies) were used as primary antibodies. Horseradish peroxidase (HRP)-conjugated IgG antibody (1:1000, Dako) was used as the secondary antibody.

Effect of the stimulation with cytokines IFNγ and TNFα on AMSCs: AMSCs isolated by adipose tissues were tested using specific surface markers by flow cytometry: the tested AMSCs were almost completely negative for the hematopoietic markers (CD34 and CD45) and >95% positive for the mesenchymal stem cells markers (CD29, CD73, CD90 and CD105) (Supplementary FIG. 1). To determine whether inflammatory stimuli may affect morphology and viability of AMSCs, cells were cultured in the presence of IFNγ/TNFα at concentration of 10, 20 and 40 ng/ml for 48 hours. Treatment with cytokines induced morphological changes, since the cells become more elongated and are characterized by an irregular shape (FIG. 1 (A)).

Figure 2:
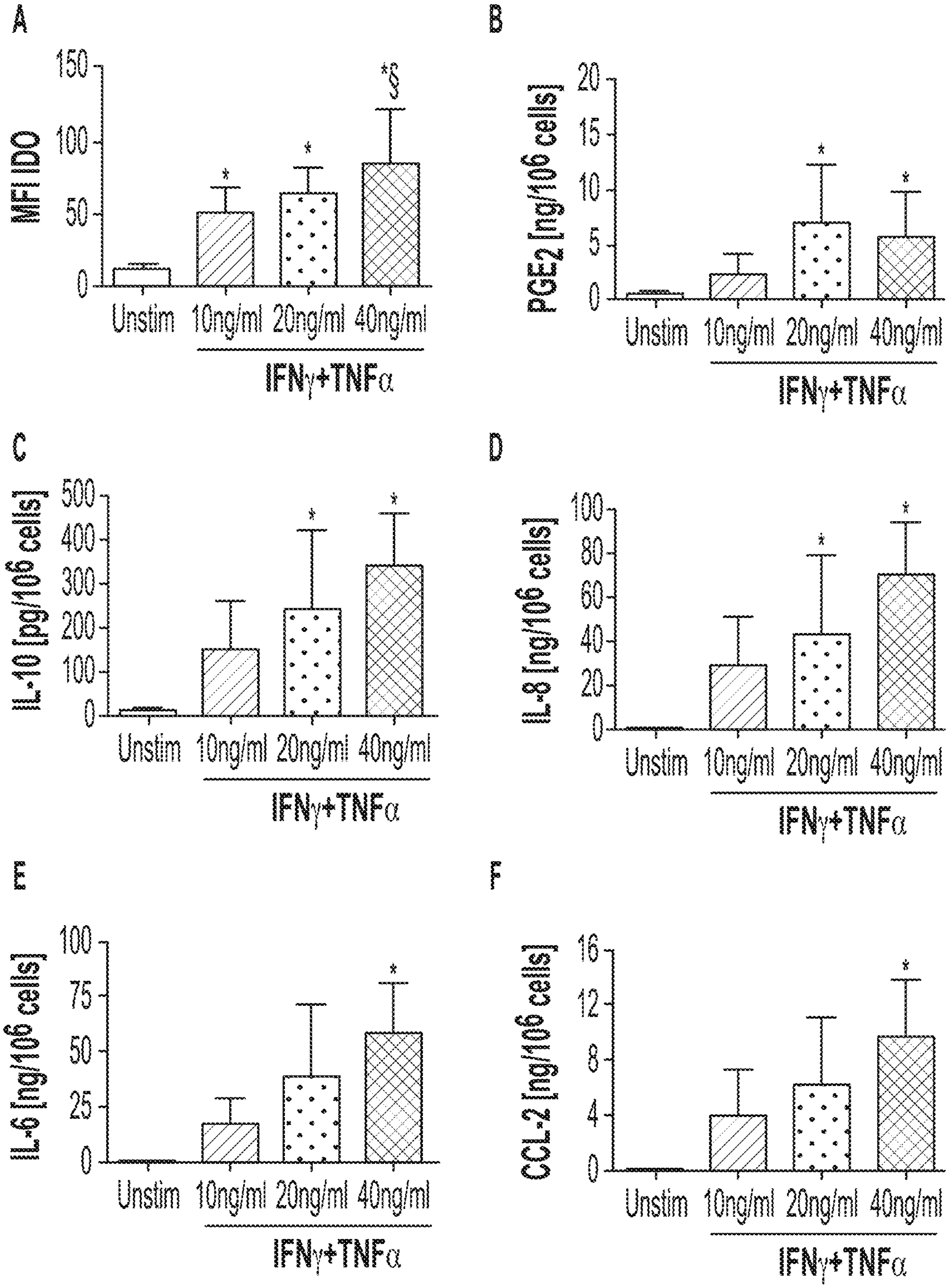
FIG. 2 depicts results illustrating that stimulation with IFNγ/TNFα mixture induces the expression of immunosuppressive factors, cytokines and chemokines in AMSCs. AMSCs were treated with IFNγ/TNFα at concentration of 10, 20 and 40 ng/ml for 48 h. Expression of IDO was determined by flow cytometry while PGE2 and cytokines/chemokines production was measured in supernatants by ELISA kit. Columns, mean; bars, SD, *significant difference from unstimulated cells, § significant difference from treatment with IFNγ/TNFα at concentration of 10 ng/ml, $P<0.05$.

The incubation with cytokines decreased AMSCs proliferation in a concentration-dependent manner (FIG. 1 (B)), while cells viability was not affected (FIG. 1 (C)). The effect of inflammatory stimuli on the release of immunosuppressive factors and cytokines/chemokines by AMSCs was examined. Treatment with IFNγ/TNFα increased the expression of the enzyme IDO in a concentration-dependent manner (FIG. 2, (A)), while the release of PGE2 (FIG. 2 (B)), IL-10 (FIG. 2 (C)) and IL-8 (FIG. 2 (D)) was significantly induced only after treatment with at least 20 ng/ml of the IFNγ/TNFα mixture. Finally, TL-6 (FIG. 2 (E)) and CCL-2 (FIG. 2 (F)) upregulation was significant only after treatment with 40 ng/ml of IFNγ/TNFα.

Figure 3:
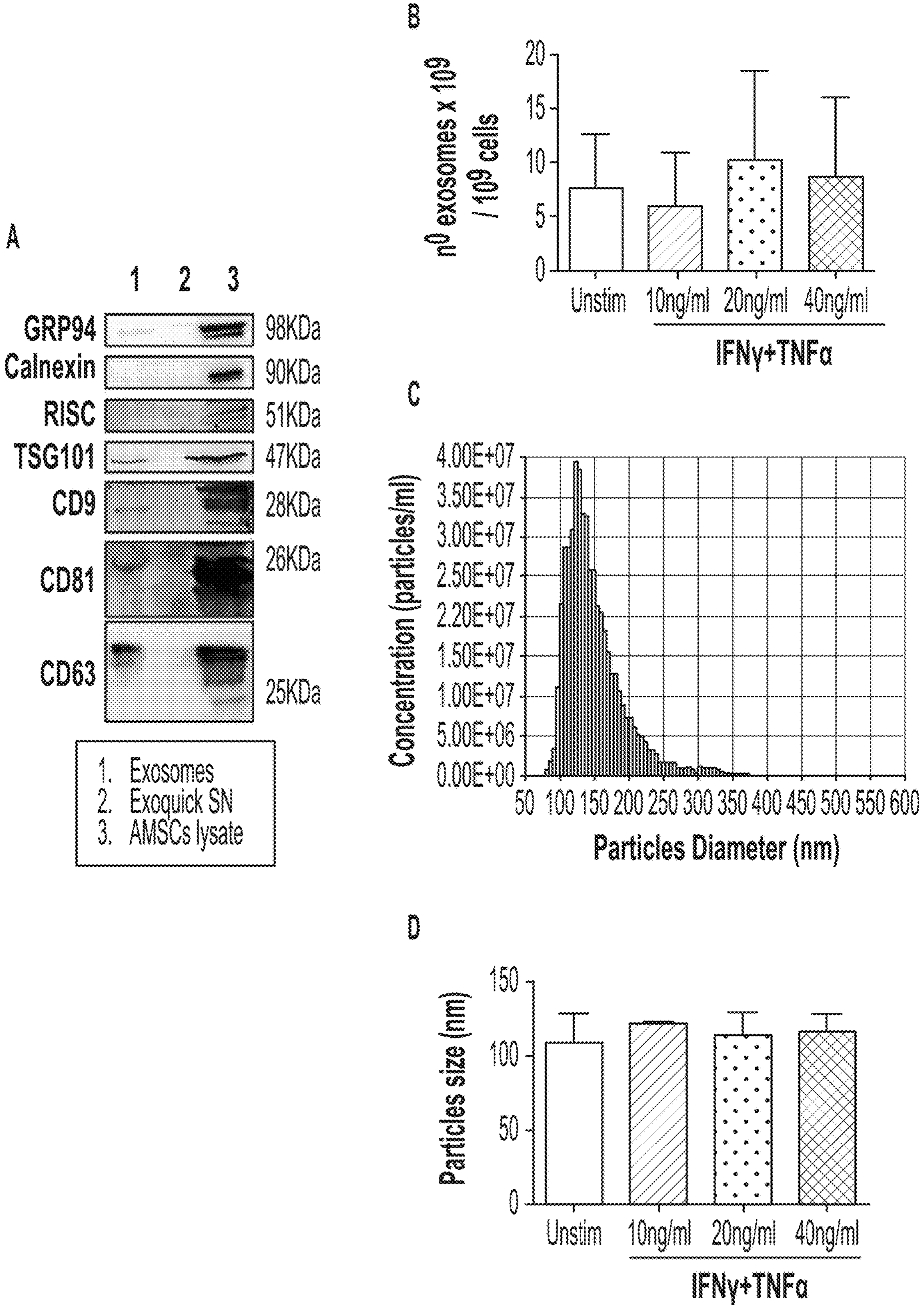
FIG. 3 depicts results that characterize AMSCs derived-exosomes. (A) Immunoblotting of AMSCs-derived exosomes, Exoquick-derived supernatants (SN) and AMSCs lysate for CD9, CD63, CD81 and TSG101 exosomal protein and Calnexin, GRP94 and RISC contaminants. (B) The concentration of exosomes was quantified measuring the enzymatic activity of the exosomal AChE enzyme by Exocet kit. Particles size were quantified by qNano system (D) and a representative graph of frequency size distribution is shown (C). Columns, mean; bars, SD.

Characterization of AMSCs derived-exosomes after stimulation by pro-inflammatory cytokines: AMSCs were pre-treated with IFNγ/TNFα at increasing concentration (10, 20 and 40 ng/ml), then an enriched fraction of exosomes was obtained from the supernatants using the Exoquick polymer-based strategy. As shown in FIG. 3 (A), AMSCs-derived exosomes and AMSCs lysates expressed the specific exosomal markers CD9, CD63, CD81 and TSG101, while no signal was observed for Exoquick-derived supernatant samples, that were used as negative control. In order to evaluate the impurities in the exosome preparations, the expression of proteins associated with subcellular compartments was assayed. These proteins are supposed to be absent or under-represented in exosomes. The lack of calnexin (endoplasmic reticulum protein) and RISC complex (nucleus protein) in exosome fraction indicates successful enrichment. A faint band for GRP94 (endoplasmic reticulum protein) also appears in the exosomal fraction, probably due to a slight contamination by apoptotic bodies.

The concentration of AMSCs-derived exosomes was determined measuring the activity of AChE by Exocet kit. As reported in FIG. 3 (B), the mean concentration of exosomes released by untreated cells was $7.6\pm2.6\times10^9$ per million of producing cells, with a size distribution shown in FIG. 3 (C). Treatment with cytokines did not influence the number of exosomes released by AMSCs. Finally, the average size of the collected vesicles, determined by qNano technology, was 115±11.5 nm, in range with exosomes proper size, and was not influenced by AMSCs cytokines treatment (FIG. 3 (D)).

Figure 4:
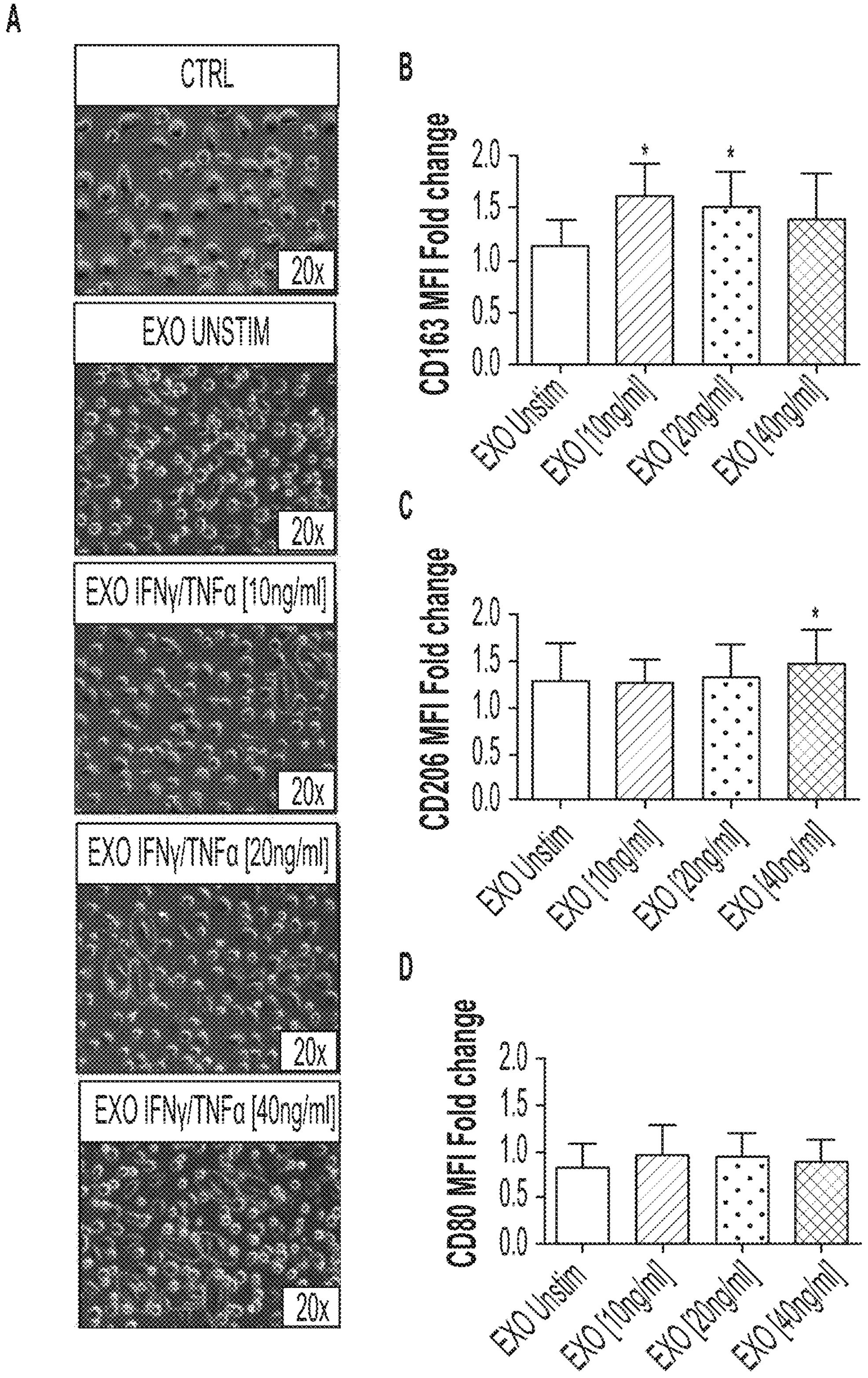
FIG. 4 depicts results illustrating that exosomes derived from AMSCs pre-activated with pro-inflammatory cytokines induce an anti-inflammatory M2 phenotype reverting M1 differentiation. (A) Representative phase contrast microscopic images (20× magnification) of monocytes differentiated into macrophages in presence of GM-CSF alone (CTRL) or in combination with exosomes isolated from the supernatants of unstimulated (EXO UNSTIM) or cytokines-activated (EXO IFNγ/TNFα 10, 20 and 40 ng/ml) AMSCs. The green circles evidence cells with elongated, spindle-like morphology, a typical feature of M2 macrophages. Flow cytometry analysis of cell surface molecules CD163 (B) CD206 (C) and CD80 (D) on macrophages. The levels of expression are presented as median fluorescent intensity (MFI) fold change respect untreated cells. Columns, mean; bars, SD, *significant difference from unstimulated cells, P<0.05.

Exosomes derived from AMSCs pre-activated with pro-inflammatory cytokines induce an anti-inflammatory M2 phenotype reverting M1 differentiation: To examine the ability of AMSCs-derived exosomes in inducing anti-inflammatory phenotype in macrophages, CD14+ monocytes isolated from PBMCs of blood donors were induced to differentiate into M1 macrophages with GM-CSF in presence of exosomes isolated from supernatants of AMSCs pre-activated with IFNγ/TNFα. As shown in FIG. 4 (A), at day 9, control monocytes gave rise to "fried egg-shaped" morphology, a typical feature of M1-like macrophages. When monocytes were differentiated in the presence of exosomes obtained from pre-activated AMSCs, some cells displayed an elongated, spindle-like morphology, a typical feature of M2 macrophages. The effect is particularly evident in monocytes incubated with exosomes isolated from AMSCs pre-activated with 40 ng/ml of IFNγ/TNFα. Indeed, compared to untreated M1-like macrophages, only exosomes isolated from pre-activated AMSCs are able to upregulate the expression of the M2 macrophage marker CD163 (FIG. 4 (B)). With regard to CD206 expression, it became significant only after treatment with exosomes produced by pre-activated cells with 40 ng/ml of IFNγ/TNFα (FIG. 4 (C)). In contrast, the expression of the M1 macrophage marker CD80 did not change significantly in the presence of AMSCs-derived exosomes (FIG. 4 (D)).

In order to evaluate possible contamination of IFNγ and TNFα in exosome preparations, the culture medium supplemented with cytokines at different concentrations (10, 20 and 40 ng/ml) was treated with Exoquick and concentration of IFNγ and TNFα was measured by magnetic beads-based multiplex assay.

These tests revealed only trace amounts of IFNγ (0.096±0.003 pg/ml) and TNFα (0.039±0.001 pg/ml), which are minimal compared to those used in literature to stimulate monocytes or macrophages. Moreover, these contaminants did not influence macrophages polarization in the expression of CD80 and CD163.

Exosomes derived from AMSCs pre-activated with inflammatory cytokines contained miRNAs involved in M2 macrophages polarization: Exosome-associated microRNAs were profiled using small RNA next generation sequencing, setting exosomes released by untreated cells as control samples and exosomes released by AMSCs treated with 20 ng/ml IFNγ/TNFα as test samples. The fold change was calculated dividing the normalized gene expression profile of test samples by the corresponding control samples. The activation with cytokines of AMSCs induced, in the released exosomes, the over-expression and the under-expression of 23 different miRNAs.

Next, RNA sequencing focused on specific miRNAs involved in the regulation of macrophage polarization. The expression of miRNAs regulating the differentiation towards M1 (miR-127-3p and miR-155-5p) or M2 (miR-34a-5p, miR124-3p, miR135b-5p and miR146a-5p) phenotypes was evaluated by quantitative RT-PCR. Of note, miR-21-5p is able to redirect both M1 and M2 polarization, depending on protein target. All the miRNAs under investigation were expressed at low level in unstimulated AMSCs-derived exosomes (FIG. 6), except for miRNA-124-3p, which was undetectable (data not shown). The expression of miRNA-34 (FIG. 5 (A)) and miRNA-146 (FIG. 5 (B)) was significantly higher in exosomes produced by AMSCs pre-activated with 20 and 40 ng/ml IFNγ/TNFα compared to those of untreated cells, while miRNA-21 expression was significantly upregulated only for 40 ng/ml cytokine pre-stimulation (FIG. 5 (C)). No difference was observed for the expression of miR-135 (FIG. 5 (D)). The expression of miR-127 (FIG. 5 (E)) and miR-155 (FIG. 5 (F)) were significantly increased only in exosomes produced by AMSCs activated with the highest (40 ng/ml) cytokine concentration, but at a very lesser extent compared to the other described miRNAs.

Figure 5:
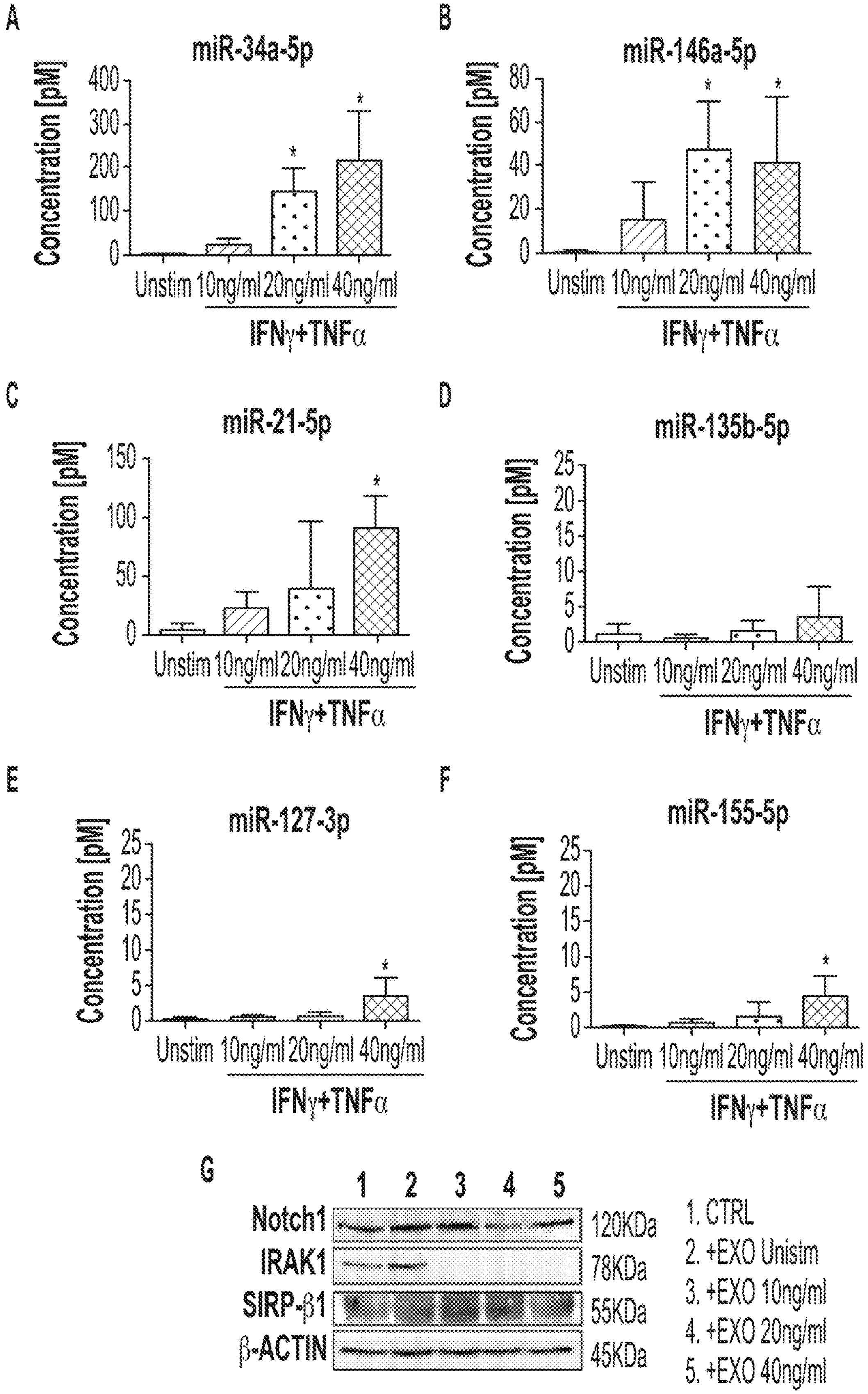
FIG. 5 depicts results illustrating that exosomes derived from AMSCs pre-activated with inflammatory cytokines contained miRNA involved in M2 macrophages polarization. The concentration of miR-34 (A), miR-127 (B), miR-21 (C), miR-135 (D), miR-146 (E) and miR-155 (F) was measured in exosomes produced by AMSCs treated with or without 10, 20 and 40 ng/ml IFNγ/TNFα by qRT-PCR. Columns, mean; bars, SD, *significant difference from exosomes of unstimulated cells, P<0.05. (G) Monocytes were differentiated in macrophages with GM-CSF in presence of exosomes isolated from the supernatants of unstimulated (EXO UNSTIM) or cytokines-activated (EXO IFNγ/TNFα 10, 20 and 40 ng/ml) AMSCs. Cell lysates were subjected to Western blot analysis with specific antibody against to IRAK1, Notch1, Sirp-β1 and β-actin.

Finally, to evaluate the downstream effect of miRNA expression upregulation in the AMSC experimental model, protein expression was analyzed for some specific miRNA targets in macrophage lysates. In particular, expression of Notch1 (targeted by miR-34a21), IRAK1 (targeted by miR-14622), and Sirp-(31 (targeted by miR-2123) were analyzed. As illustrated in FIG. 5 (G), IRAK1 expression was dramatically reduced after treatment with exosomes of pre-stimulated AMSCs, while the expression of Notch1 was reduced only with exosomes release from cells treated with 20 ng/ml of cytokines. The expression of Sirp-(31 was not affected by the treatment with exosomes.

Tumor Cell culture and LPS treatment: The human tumor cell lines SW480 (primary colon adenocarcinoma), SW620 (metastatic colon adenocarcinoma), MDA-MB-231 (metastatic breast adenocarcinoma) and U87-MG (glioblastoma) were purchased from Sigma-Aldrich. Cells were grown in two different Dulbecco's modified essential media (DMEM high glucose for SW480 and SW620 and DMEM low glucose for MDA-MB-231 and U87-MG) (Sigma-Aldrich) supplemented with 10% FBS (Gibco) and 1% penicillin/streptomycin solution (Gibco) at 37° C. with 5% $CO_2$ in humidified air.

To activate TLR4, cells were incubated with [1 μg/ml] LPS (*E. coli* 055:B5 LPS, Sigma-Aldrich) for 24 hours, washed three times with PBS and then culture medium was replaced with fresh medium supplemented with 10% certified exosomes-free serum (Gibco). After 24 hours, supernatants were collected and stored at −20° C. until use, while cells were harvested, and their proliferation/viability was determined by the trypan blue exclusion assay.

Exosome isolation and characterization: Exosomes were isolated from the supernatants of the cell lines with the polymer precipitation method with ExoQuick-TC (System Biosciences. The exosomes-containing pellet was resuspended in PBS or lysis buffer for subsequent analysis. The number of exosomes was determined using the Exocet kit (System Biosciences), according to the manufacturer's instructions, and size distribution was evaluated by nanoparticles tracking analysis (NTA) with the Nanosight LM10 system (Malvern Instrument Ltd.) equipped with a 532 nm laser.

Cells lysate, exosomes and Exoquick-derived supernatants were analysed for the expression of exosomal markers and contaminants by immunoblotting. Human anti-CD9 (1:1000, System Bioscience), anti-CD63 (1:1000, LS Bio), anti-CD81 (1:500, Abcam), anti-TSG101 (1:500, Abcam), anti-calnexin (1:1000, Enzo Life Technologies), anti-GRP94 (1:1000, Genetex) and anti-RISC (1:1000, Abcam) were used as primary antibodies. As a secondary antibody anti-IgG antibody conjugated with horseradish peroxidase was used.

Exosomes were also purified by immunoaffinity Exo-Flow kit (System Biosciences), stained with Exo-FITC provided by the kit or specific monoclonal antibodies anti-CD81 FITC (Biolegend), anti-CD63 FITC (Santa Cruz), anti-CD9 PE (eBiosciences), anti-MICA/B Alexa Fluor 488 (Invitrogen) and anti-ULBP-1 APC (Invitrogen) and analysed by flow cytometry.

The expression of TGF-β isoforms was quantified using the TGF-β Magnetic Luminex Performance Assay kit (R&D Systems). Exosomes ($1\times10^8$) were activated with HCl, neutralized and diluted in RD6-50 buffer, according to the manufacturer's instructions, and subsequently analysed on a Bio-Plex 200 system (Bio-Rad).

Labelling of tumor exosomes: To investigate the ability of CD14+ monocytes and CD3+ T cells to internalize tumor exosomes, vesicles were labelled with DiD (Invitrogen), according to the manufacturer's instructions. Briefly, $1\times10^{10}$ exosomes were resuspended in PBS and stained with 5 M DiD for 30 minutes at 37° C. DiD labelled exosomes were incubated with $2\times10^5$ isolated PBMCs for 6, 14, 24, 18 hours and then cells were analysed by flow cytometry by gating either on CD14+ or CD3+PBMCs.

Isolation of the T cell population: For the in vitro experiments, samples of whole blood from healthy donors were collected in EDTA-tubes by the Department of Transfusion Medicine (University Hospital of Udine), after obtaining an informed consent.

Human peripheral blood mononuclear cells (PBMCs) were separated by centrifugation at 700×g for 20 minutes on a Ficoll Hypaque density gradient (Millipore) and resuspended at $1\times10^6$ cells/ml in RPMI 1640 complete medium supplemented with 10% FBS, 1% glutamine, 1% Na pyruvate, 1% non-essential amino acid, 1% penicillin/streptomycin, 1% Hepes (all from Sigma-Aldrich). To remove the exosomal fraction present in FBS, serum was always ultracentrifuged for 4 hours at 100,000×g.

CD16+/CD56+NK and CD4+ T cells were purified from PBMCs by negative selection using immunomagnetic beads (StemCell Technologies), according to the manufacturer's instructions. The efficiency of the purification was over 95% as assessed by staining with specific antibodies and flow cytometric analysis (FACSCalibur).

CFSE proliferation assay: PBMCs were labelled with 5 M carboxyfluorescein succinimidyl ester (CFSE, Invitrogen) in PBS with 0.1% bovine serum albumin for 10 minutes at 37° C., followed by immediate quenching with cold culture medium. To determine the immunomodulatory effect of exosomes on PBMCs, $2\times10^1$ cells resuspended in 200 μl of medium were preincubated for 24 hours with $5\times10^9$, $5\times10^8$, $5\times10^7$ and $5\times10^6$ exosomes produced by tumor cells, then seeded into 96 well-plates with pre-bound 0.5 μg/ml anti-CD3 (clone OKT3, eBiosciences) and 0.5 μg/ml anti-CD28 (clone CD28.6, eBiosciences). After 3 days, in vitro stimulated PBMCs were stained with anti-CD3 APC, anti-CD4 APC or anti-CD8 APC (all from eBiosciences) and cell proliferation was tested by flow cytometry.

Treg cell induction: Isolated CD4+T lymphocytes were incubated with $5\times10^8$ exosomes and stimulated with anti-CD3 and anti-CD28 in the concentrations described above. The recombinant IL2 at the concentration of 250 U/ml was also added as a stimulus. After 3 days, the percentage of FoxP3+ regulatory T cells in the total population of stimulated CD4+ cells, was determined by CD25 surface staining and FoxP3 intracellular staining using Foxp3/Transcription Factor Staining Buffer Set (eBiosciences).

NKG2D expression levels: Resting PBMCs or purified NK cells obtained from healthy donors were co-incubated with or without $5\times10^8$ exosomes for 24 hours, then cells were stained with anti NKG2D APC and anti-CD8 FITC or anti-CD16 FITC/anti-CD56 PE (all from eBiosciences) and tested by flow cytometry.

Exosomal RNA isolation and RT-PCR: To preserve small RNAs, total RNA was extracted from $1\times10^{10}$ exosomes, using mirVana PARIS Kit (Life Technologies), adding cel-miR39 spike-in as exogenous control (100 μM) (ThermoFisher Scientific). The extracted RNA was stored at −80 until use. Its quantity and quality have been evaluated with the NanoDrop™ 1000 Spectrophotometer (ThermoFisher Scientific).

The relative concentrations of miRNAs (has-miR-21-5p, has-miR-155-5p, and has-miR-34a-5p) were assessed using the TaqMan® Advanced miRNA Assays (ThermoFisher Scientific), according to the manufacturer's instructions, except for cDNA templates that were diluted 1:2 instead of the recommended dilution of 1:10.

Real-time reaction was performed on the Applied Biosystems QuantStudio 3 System. miRNA relative concentrations were normalized using relative standard curve method obtained by serial dilutions of cel-miR39 (1 nM-100 fM).

Validation of exosomes released by tumor cells upon TLR4 activation by LPS: Tumor cells were pre-treated with LPS, then an enriched fraction of exosomes was obtained from the supernatants using the Exoquick polymer-based method.

Figure 6:
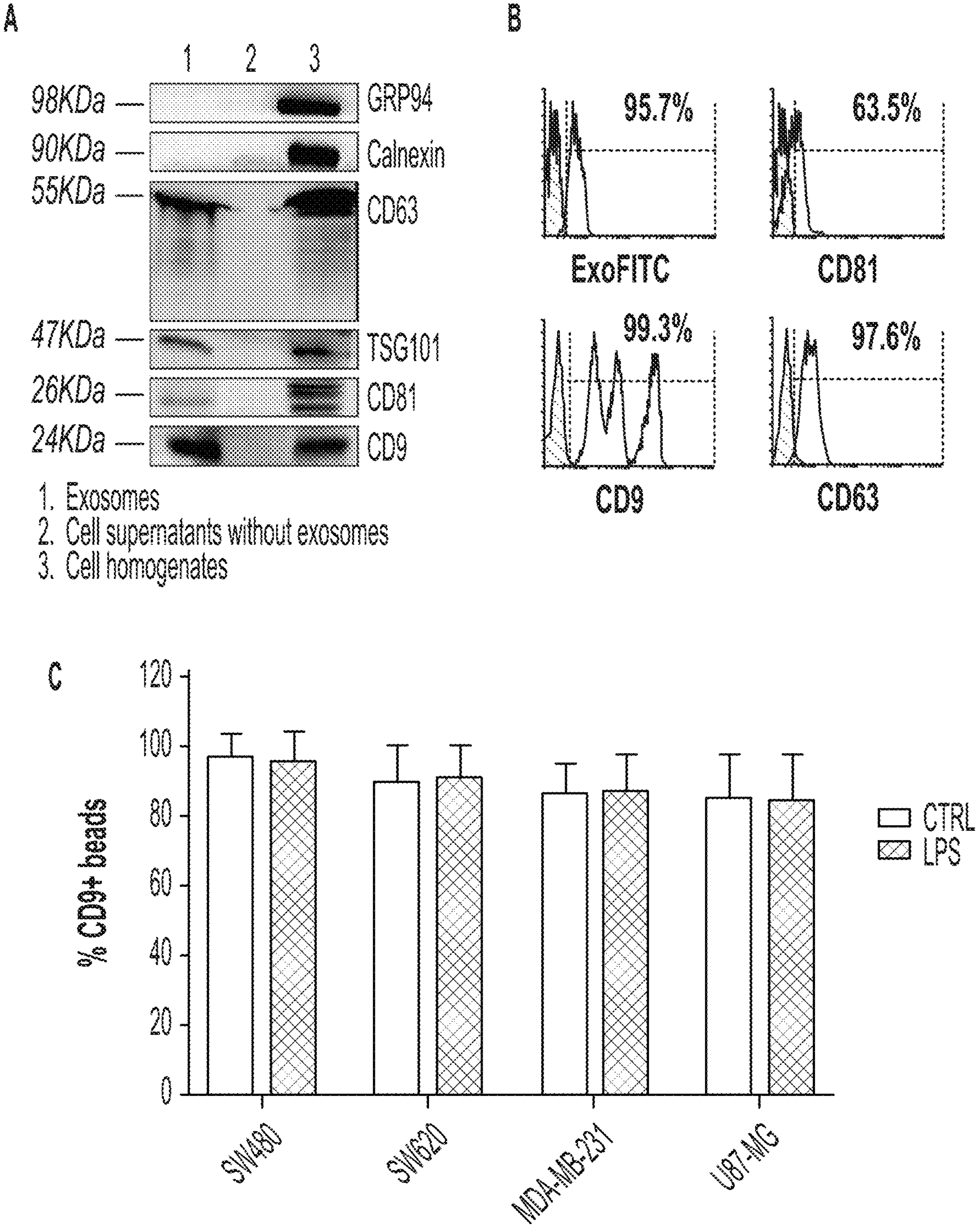
FIG. 6 depicts results that characterize exosomes from stimulated tumor cells; (A) Immunoblot analysis of tumor-derived exosomes, Exoquick-derived supernatants and cells homogenates probed for the indicated proteins. (B) Exosomes were coupled to ExoFlow beads, stained with ExoFITC dye or specific monoclonal antibody for CD81, CD9, and CD63 and analyzed by flow cytometry. The antibodies (white peak) were compared with their appropriate isotype control (grey peak). Histograms from one representative experiment are shown. (C) The histogram represents the percentages of CD9-positive beads bound to exosomes released by unstimulated (CTRL, white column) or LPS-activated cells (LPS, black column). Data are shown as mean (n=4)±SD. (D) The number of exosomes was estimated measuring the enzymatic activity of the exosomal AChE enzyme by Exocet kit (D) or by nanoparticle tracking analysis (NTA) by LM10 Nanosight (E) Data are shown as mean (n=8)±SD. *P<0.05. (F-G) The particles size distribution was evaluated by Nanosight and a representative graph of frequency size distribution is shown. Data are shown as mean (n=8)±SD. *P<0.05.
Figure 6:
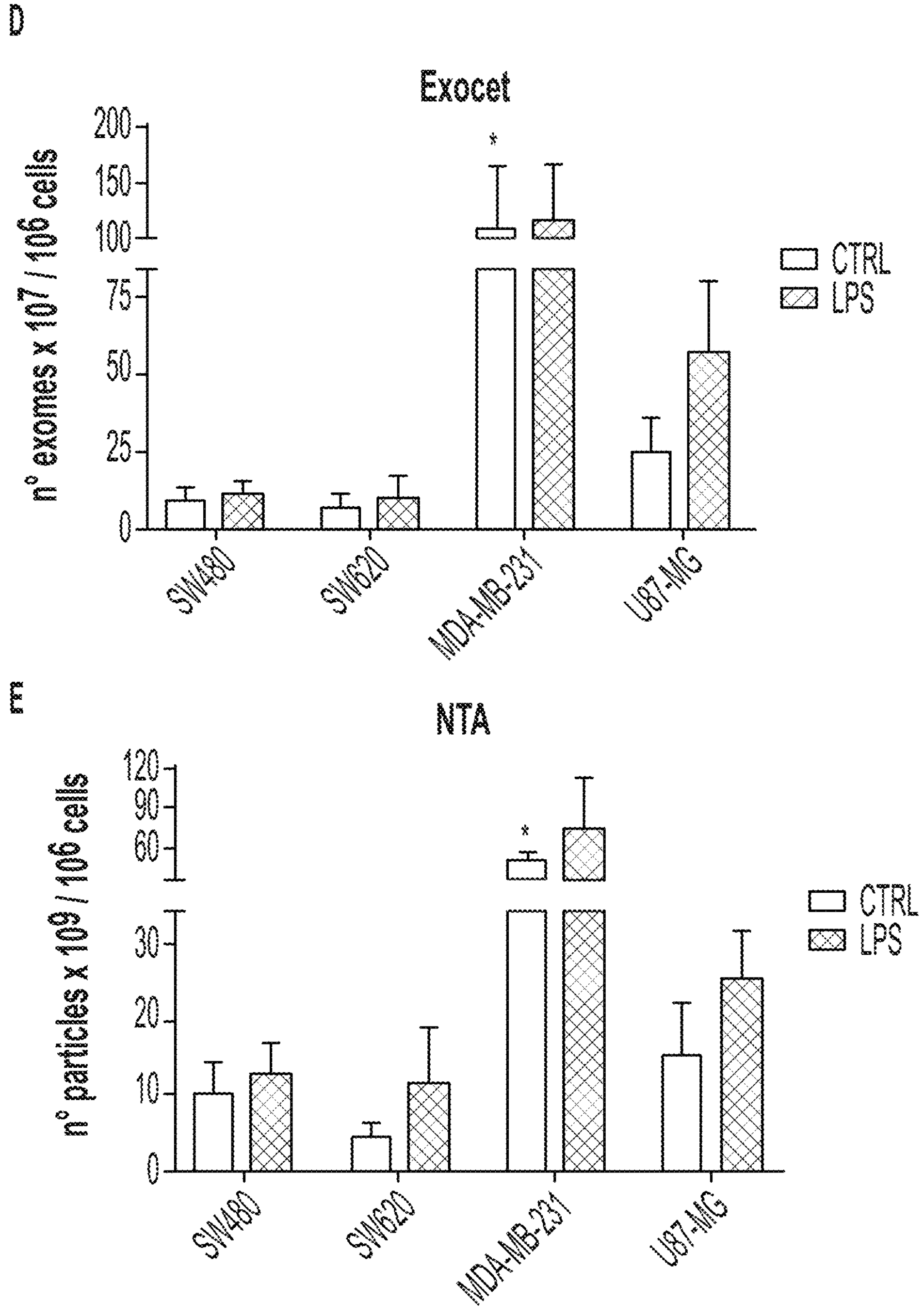
Figure 6:
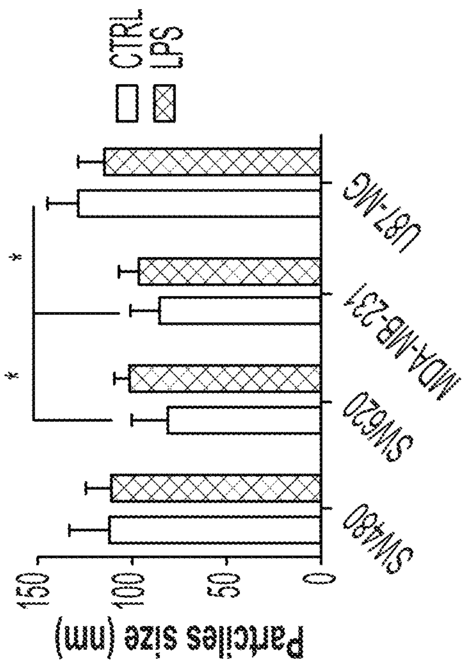
Figure 6:
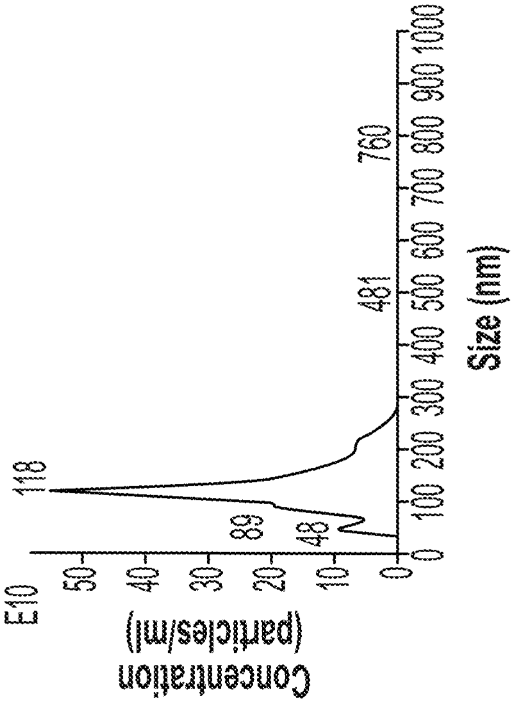

As shown in FIG. 6 (A), exosomes and cell lysates expressed the specific exosomal markers CD63, TSG101, CD81 and CD9, while no signal was observed with the Exoquick-derived supernatants, which were used as negative controls. To evaluate impurities in the exosomes preparations, the expression of proteins associated with subcellular compartments was assayed. These proteins are supposed to be absent or under-represented in exosomes. The lack of calnexin and GRP94 (endoplasmic reticulum proteins), indicated a successful enrichment. The expression of exosomal markers was further confirmed by flow cytometric analysis of exosomes coupled to Exo-Flow beads. As shown in FIG. 6 (B), beads bound to exosomes expressed high levels of CD81, CD9 and CD63 and reacted with the ExoFITC reagent. It is interesting to note that the expression profile of CD9 highlighted the presence of three distinct exosomes subpopulations and its expression did not change after the treatment with LPS (FIG. 6 (C)).

The concentration of exosomes released by tumor cells was determined measuring the activity of AChE with the Exocet kit (FIG. 6 (D)) and by Nanoparticle tracking analysis (NTA) (FIG. 6 (E)). These quantification methods provided different absolute values, probably due to the different principle on which the respective analyzes are based. Specifically, NTA analysis reported a concentration of about 100 times higher than that measured with the Exocet kit. However, both quantification methods showed that cellular activation with LPS by stimulation of TLR4 did not influence the number of exosomes released, although a slight non-significant increase, was observed for exosomes produced by U87-MG. It is interesting to report that untreated MDA-MB-231 cells released the highest number of exosomes.

As reported in the dimensional profile of the representative NTA analysis (FIG. 6 (F)), tumor exosomes are detected as nanoparticles with dimensions comparable to those described for physiological exosomes (range from 50 to 120 nm in diameter). Specifically, the average size of the collected vesicles was 113±21.1 nm for SW480-derived exosomes, 81.5±19.7 for SW620-derived exosomes, 86.4±15.1 for MDA-MB-231-derived exosomes and 129±16.1 for U87-MG. Finally, the size of exosomes was not influenced by LPS treatment of producing cells (FIG. 6 (G)).

Figure 7:
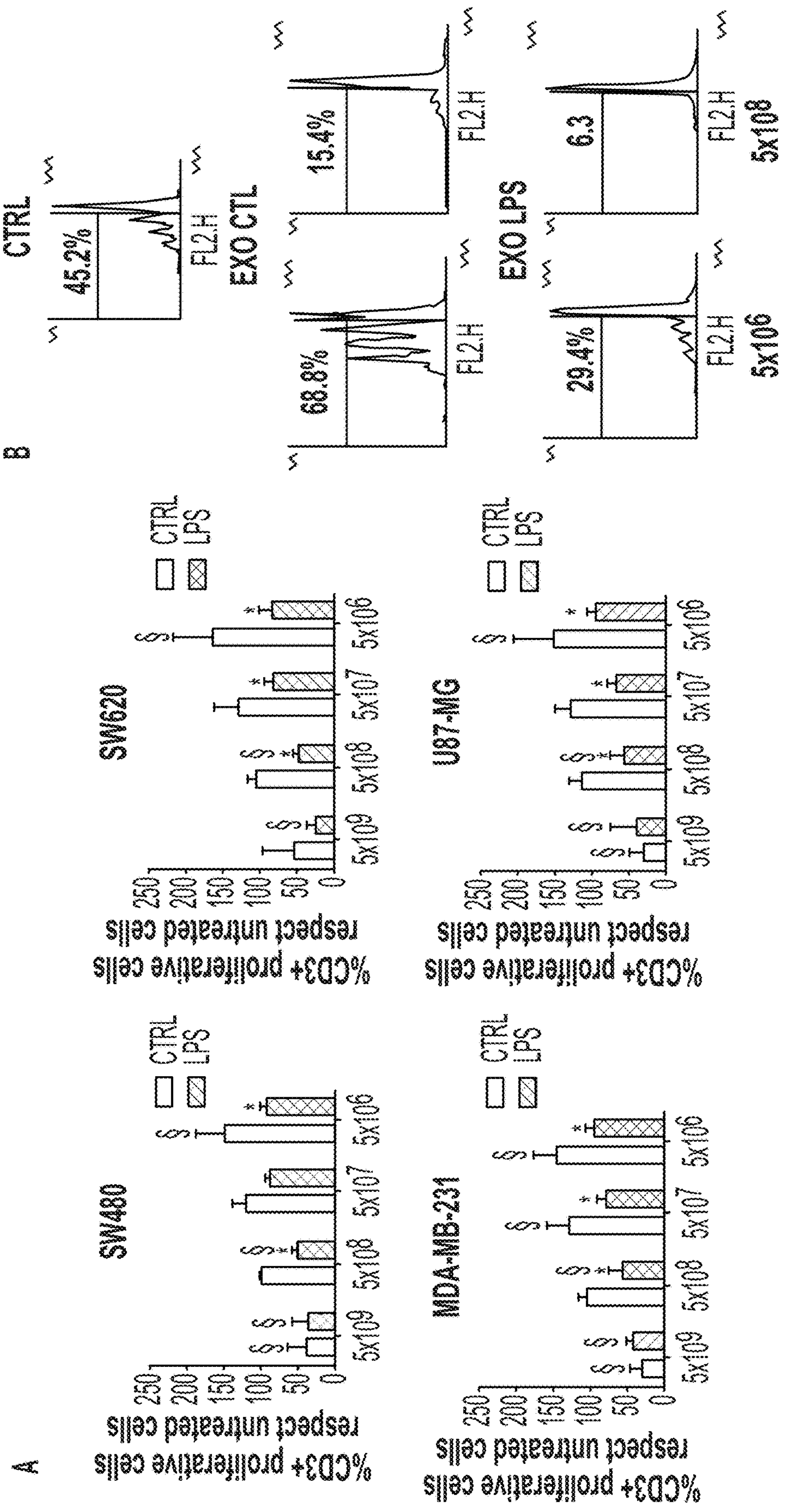
FIG. 7 depicts results illustrating that exosomes released after LPS treatment inhibit T cell proliferation in a dose-dependent manner; (A) CFSE-labeled PBMCs isolated from healthy donors were pre-treated for 24 hours with scalar doses (from $5\times10^6$ to $5\times10^9$) of exosomes released by unstimulated (CTRL, white column) or LPS-activated tumor cells (LPS, black column). Histograms show the percentage of CD3+ T cells in proliferation, assigning the value of 100% to the proliferation activity of untreated cells. Data are shown as mean (n=5)±SD. § P<0.05 compared to untreated CD3+ T cells; *P<0.05 compared to the proliferation of CD3+ T cells treated with exosomes released by unstimulated tumor cells; (B) Representative cytometry CFSE histograms show the proliferative fraction of untreated (CTRL) and exosomes-treated (EXO CTRL and EXO LPS) CD3+ T cells. CFSE-labeled PBMCs were pretreated for 24 hours with $5\times10^8$ exosomes and histograms show, within the PBMCs, the fraction of proliferating CD3+(C), CD4+(D) and CD8+(E) T cells, considering the proliferation of untreated cells as 100%. Data are shown as mean (n=6)±SD. *P<0.05.
Figure 7:
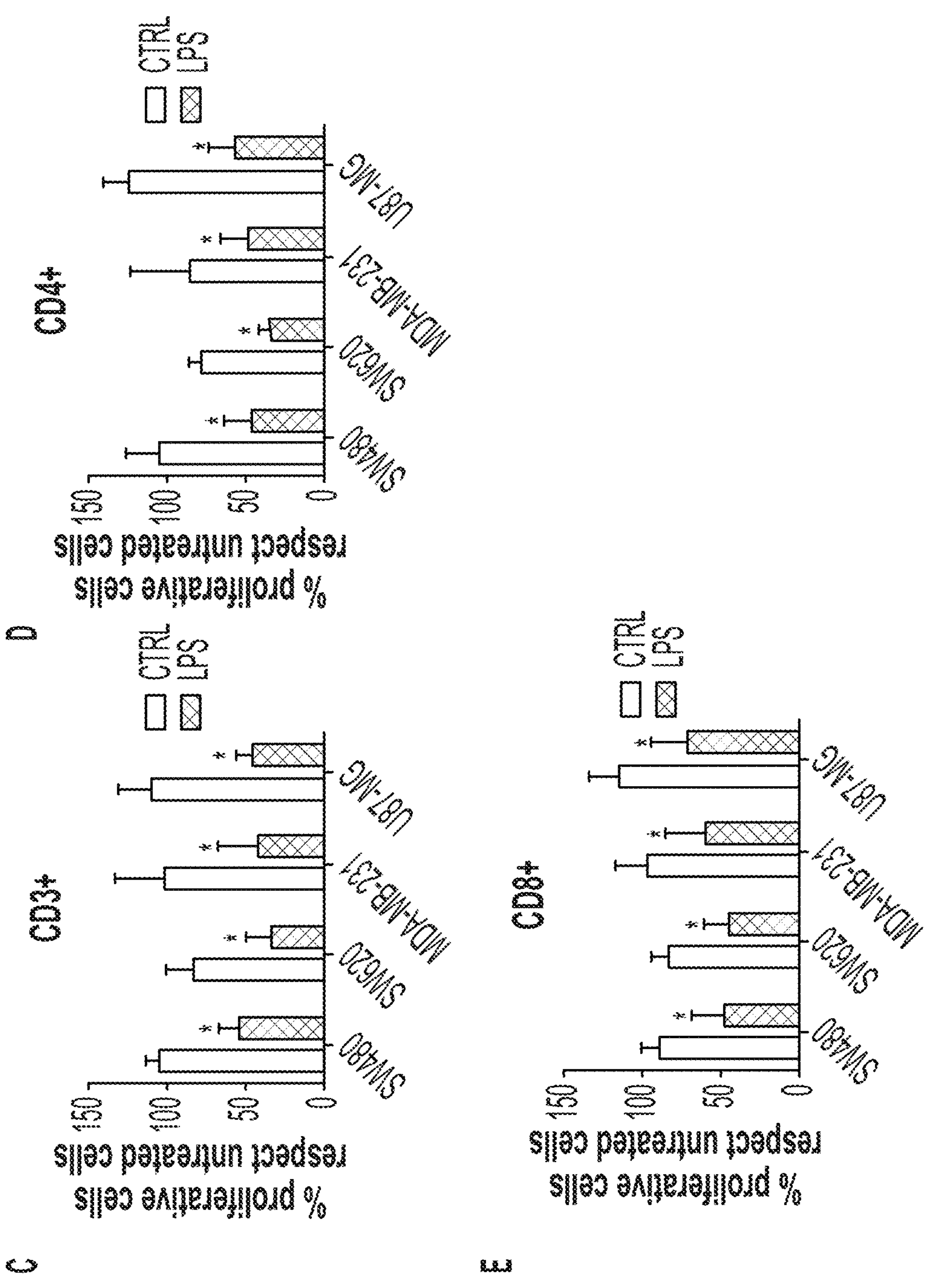

Exosomes released upon LPS treatment inhibit T cell proliferation in a dose-dependent manner: To determine whether activation of TLR4 expressed on tumor cells influences the immune-modulatory properties of released exosomes, CFSE-labelled PBMCs, isolated from healthy donors, were incubated for 24 hours with scalar doses (from $5\times10^6$ to $5\times10^9$) of exosomes and then stimulated with plate-bound anti-CD3 and soluble anti-CD28. Only exosomes released upon LPS treatment, up to $5\times10^8$, significantly inhibited CD3+ T cell proliferation in a dose-dependent manner. In all other cases, only the highest dose ($5\times10^9$) of exosomes released by the untreated cells was able to inhibit the proliferation of CD3+ T cells. With lower doses, the inhibitory effect of the exosomes released by the unstimulated cells disappeared, while a stimulation effect on T cell proliferation appeared (FIG. 7 (A)(B)).

In order to evaluate the effect of the exosomes on the proliferation of different T cell subtypes, the PBMCs were incubated with $5\times10^8$ exosomes and labeled for the expression of CD4 and CD8. As the dose of exosomes to use in the experiments, the smallest dose able to induce a different effect on the proliferation of T lymphocytes between control and LPS-treated exosomes was chosen, based on previous results. Only exosomes released after LPS treatment were able to significantly inhibit the proliferation of both, CD4+ (FIG. 7 (D)) and CD8+(FIG. 7. (E)) T cells.

Figure 8:
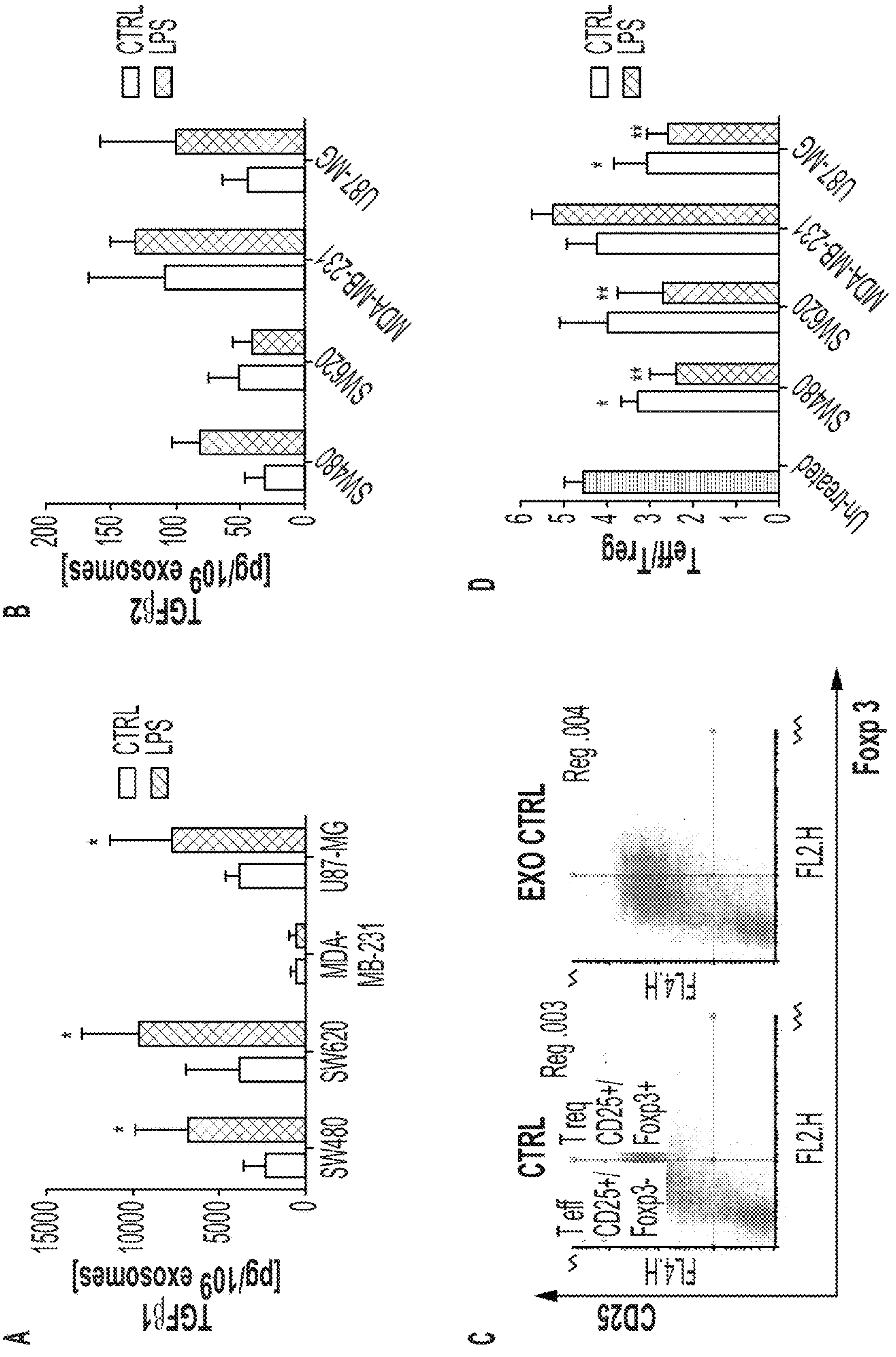
FIG. 8 depicts results illustrating expression of TGFβ on the surface of exosomes and its effect on regulatory T cells expansion. The expression of TGF-β1 (A) and TGF-β2 (B) on the surface of exosomes were evaluated using the TGF-β Magnetic Luminex Performance Assay on exosomes released by unstimulated (CTRL, white column) o LPS-activated tumor cells (LPS, black column). Data are shown as mean (n=8)±SD. *difference with exosomes released by unstimulated tumor cells, P<0.05. (C-D) CD4+ T cells, isolated from PBMCs by negative selection, were stimulated with anti-CD3, anti-CD28 and IL-2 in the presence of exosomes released by unstimulated (CTRL, white column) o LPS-activated tumor cells (LPS, black column). The percentage of effector (CD4+/CD25−/FoxP3−) or regulatory T cells (CD4+/CD25+/FoxP3+) was determined by fluorescence activated flow cytometry (FACS) on day 4. Representative plots for CD25 and Foxp3 staining are shown and histograms represent the ratio between the percentage of effector and regulatory T cells ($T_{eff}/T_{reg}$). Data are shown as mean (n=6)±SD.; *difference with the untreated cells, P<0.05; **difference with the untreated cells, P<0.005.

Expression of TGFβ on exosomes surface and its effect on regulatory T cells expansion: To investigate the molecular mechanisms underlying the inhibitory effects of exosomes released by tumor cells upon TLR4 activation by LPS, TGFβ was assayed on exosome surfaces, as this cytokine is strongly implicated in mechanisms of immune evasion and may be responsible for the antiproliferative effect observed in the study. Expression of the three different TGFβ isoforms was assayed by multiplex assay, finding that only TGFβ1 and TGFβ2 were measurable in the exosomal samples, while TGFβ3 was undetectable (data not shown). Specifically, TGFβ1 was expressed at a very low level on the surface of exosomes released by MDA-MB-231 as compared to the other cells lines (FIG. 8 (A)). Interestingly, the expression of TGFβ1 was increased in exosomes released by SW480, SW620 and U87-MG cells upon TLR4 activation by LPS, while no differences was observed for MDA-MB-231-derived exosomes. The expression of TGFβ2 on exosome surface was not influenced by cell TLR4 activation by LPS (FIG. 8 (B)).

It was hypothesized that TGFβ1 expressed on the surface of exosomes could also induce the conversion of CD4+ CD25− T cells into Foxp3-expressing regulatory T cells. Stimulation by exosomes secreted by untreated SW480 and U87-MG increased the percentage of CD4+/CD25+/Foxp3+ cells in the PBMC population (FIG. 8 (C-D)) and this stimulatory effect became statistically more significant with exosomes released by cells upon TLR4 activation. Interestingly, only exosomes produced by SW620 cells upon TLR4 activation become capable of inducing conversion to regulatory T cells.

Figure 9:
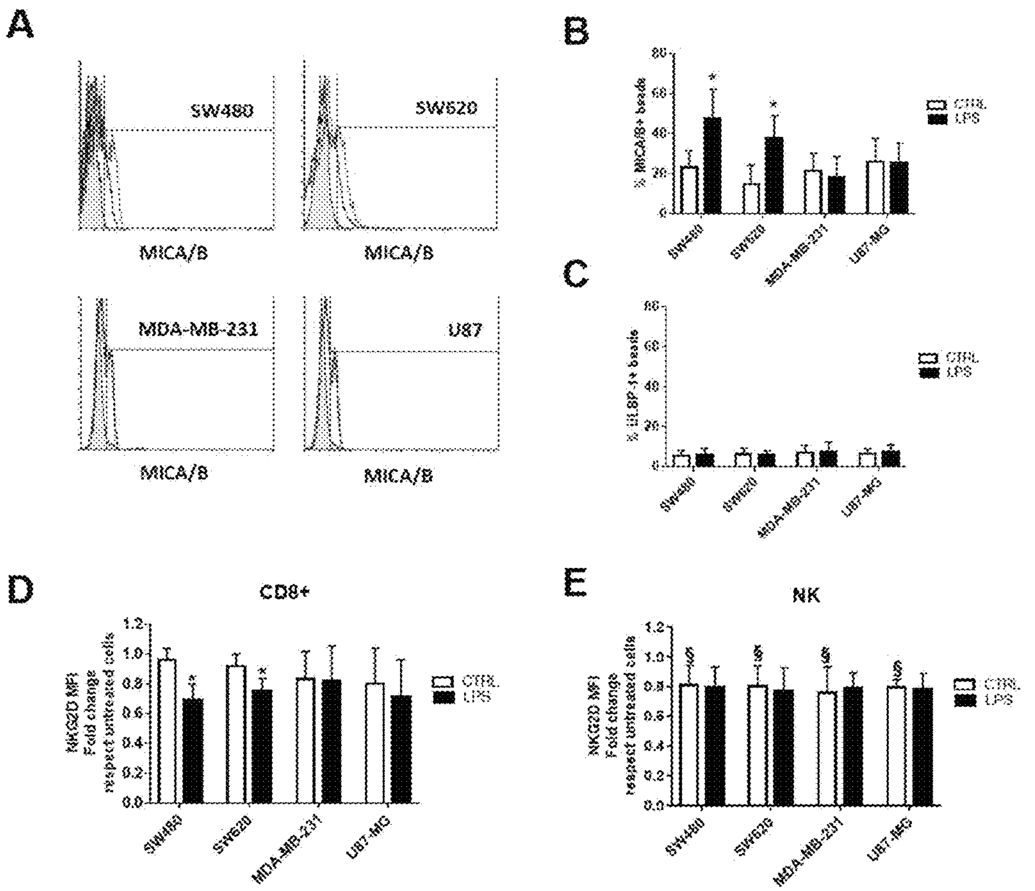
FIG. 9 depicts results illustrating expression of NKG2D ligands on the surface of exosomes and modulation of NKG2D expression on NK and CD8+ T cells; Exosomes were coupled to ExoFlow beads, stained with monoclonal antibodies either against MICA/B or ULBP-1 and analysed by FACS. (A) Representative plots of the FACS analyses for MICA/B staining of control (black line) and of LPS-derived exosomes (red line) are shown. The histograms represent the percentages of MICA/B-(B) and ULBP-1 (C)-positive beads bound to the exosomes released by unstimulated (CTRL, white column) o LPS-activated cells (LPS, black column). Data are shown as mean (n=6); bars, SD; *difference with exosomes released by unstimulated tumor cells, P<0.05. PBMCs or isolated CD16+CD56+NK cells were treated for 24 hours with exosomes released by unstimulated (CTRL, white column) o LPS-activated tumor cells (LPS, black column). Expression of NKG2D by CD8+(D) and NK cells (E) was analysed by FACS. Data are shown as mean (n=6); bars, SD; § difference with untreated cells; *difference with cells treated with exosomes released by unstimulated tumor cells, P<0.05.

Expression of NKG2D ligands on the surface of exosomes and modulation of NKG2D expression on NK and CD8+ T cells: There is mounting evidence showing that tumor cells escape immune surveillance by the release of soluble NKG2D ligands, which trigger a general downregulation of the NKG2D receptor on NK cells and CD8+ T cells. The expression of MICA/B and ULBP-1, a NKG2D ligands, on the surface of exosomes coupled to Exo-Flow beads was evaluated by FACS analysis. As shown in the representative plot of the FACS analysis, tumor exosomes expressed, even if at low levels, MICA/B (FIG. 9 (A-B)), but not ULPB-1 (FIG. 9 (C)). Interestingly, the expression of MICA/B was increased following activation of TLR4 with LPS only in the exosomes released by SW480 and SW620. Moreover, they were able to reduce the expression of NKG2D in T lymphocytes. In contrast, the expression of NKG2D in purified NK cells was slightly reduced by exosomes released from all tumor cell lines, but no further effect was observed after activation of TLR4 with LPS. (FIG. 9 (E)).

Figure 10:
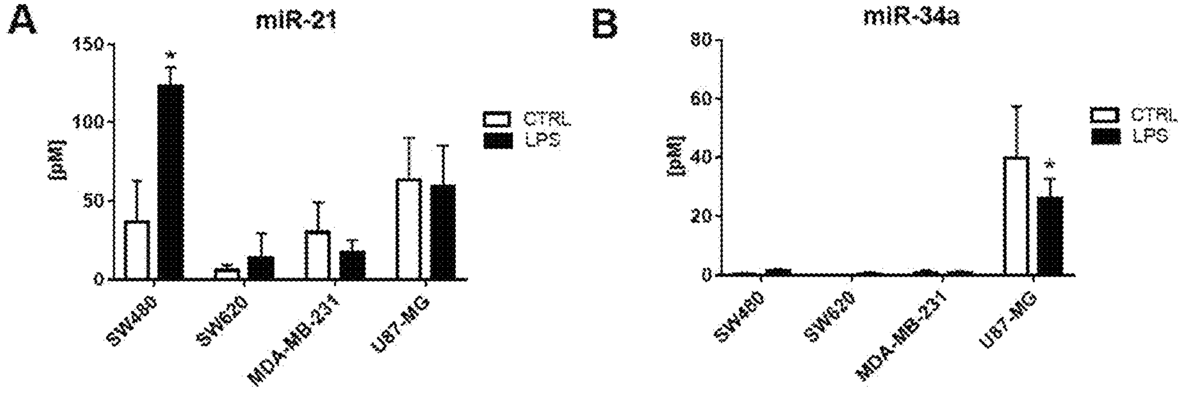
FIG. 10 depicts results illustrating expression of miR-21 and miR-34a in tumor-derived exosomes; The concentration of miR-21 (A) and miR-34a (B) was measured in exosomes produced by unstimulated (CTRL, white column) o LPS-activated tumor cells (LPS, black column) by qRT-PCR. Data are presented as mean (n=3); bars, SD, *difference with exosomes released by unstimulated tumor cells, P<0.05.

Expression of miR-21, miR-34a and miR-155 in tumor-derived exosomes: Several specific miRNAs have recently emerged as important regulators of immune-cell function in the context of different solid tumors. Among these, miR-21, miR-155, and miR-34a are mediators of immune suppression, as they promote the expression of immunosuppressive factors and regulate T cell differentiation. To analyze the expression of these miRNAs, total RNA was extracted from tumor-derived exosomes released by cells upon TLR4 activation. The expression of miRNA-21 (FIG. 10 (A)) was significantly higher in exosomes produced by SW480 pre-treated with LPS compared to exosomes from untreated cells. No difference was observed for exosomes produced by other cell lines. On the other hand, miR-34a was found only in exosomes produced by U87-MG and miR-34a expression decreased significantly after treatment with LPS (FIG. 10 (B)). Finally, no exosomes produced by any cell line analyzed showed expression of miRNA-155 (data not shown).

The data suggest that the activation of TLR4 on tumor cells did not influence the number or size of released TEXs. Instead, it increased their immunosuppressive potential. As already reported in the literature, exosomes secreted by untreated tumor cells are able to inhibit T cells proliferation. The effect, however, occurs only with high-dose treatments, while low doses stimulate the proliferation of T cells. Instead, exosomes produced by tumor cells after TLR4 activation were always immunosuppressive, suggesting that the treatment influences TEX cargo. The molecular profiles show that TEX may express a dual capability of mediating either immune suppression or immune stimulation, presumably depending upon the microenvironment. The immunostimulatory properties of TEXs released after TLR4 activation are probably due to the presence of tumor-associated antigens (TAA) and costimulatory molecules on TEX surface, which stimulate the immune response. It has been reported that exosomes produced by lymphoma cells after a heat-shock contained high levels of Hsp70 and were reported to stimulate a direct Th1-polarized immune response in a MHC-independent manner in autologous and allogeneic murine models.

Upon release from the cell surface, exosomes possess the capacity to fuse with the plasma membranes of recipient cells to deliver their content into the cytoplasm. Alternatively, proteins present on their surface can bind cell surface receptors on target cells and influence intracellular signaling. While monocytes rapidly take up exosomes, T cells do not internalize TEXs, even after 48 hours of co-incubation. Consistent with other studies that show that T lymphocytes, unlike other mononuclear cells, do not internalize exosomes, the data suggest that TEXs deliver signals to receptors present on the T cell surface. Exosomes produced by cancer cells may induce regulatory T cells growth through the TGF-β1 expressed on their surface. The data demonstrate that TLR4 activation increases the expression of TGF-β1 on TEX surface and promotes the expansion of regulatory T cells, which in turn may be responsible for the reported anti-proliferative effects of TEXs on T cells. Exosomes secreted by the breast cancer cell line MDA-MB-231 expressed TGF-β1 at a very low level, as compared to exosomes released by the other cells lines, even after TLR4 cell activation, and fail to induce regulatory T cells.

The production of NKG2D-ligand-bearing exosomes is a newly described mechanism for cancer cell immune evasion. Exosomes released by all cell lines analyzed express on their surface MICA/B, a NKG2D ligand, although TLR4 activation only increased MICA/B expression in exosomes derived from colorectal cancer its expression. It is therefore possible to hypothesize that colorectal cancer cells are more sensitive to the activation of TLR4. In fact, a correlation between the chronic activation of TLR4 and the progress of CRC through the release of immunosuppressive factors which promote tumor escape has been widely shown.

Increasing evidence suggests that exosomal microRNAs secreted by cancer cells can be delivered to other cells in the local microenvironment leading to reprogramming of the target cell transcriptome and influencing cancer growth, angiogenesis, metastasis and immune function in a paracrine manner. MiR-21 and miR-155 are well-characterized oncomiRs that promote both, cancer growth and metastasis by targeting numerous mRNAs. In contrast, miR-34a has been shown to suppress cancer growth and metastasis by inducing apoptosis, cell cycle arrest and senescence. Expression of miR-21 was increased in SW480-derived exosomes after TLR4 activation. Also, it has been demonstrated that miR-21 present in cancer cell-secreted exosomes can be transferred to surrounding immune cells and can bind to Toll-like receptors. By binding to TLRs, miR-21 induces cytokines secretion by the immune cells, leading to a pro-metastatic inflammatory response that ultimately may lead to cancer growth and metastasis.

As should be appreciated from the data presented herein, exosomes derived from cells that were previously stimulated with a pro-inflammatory (or other activating/stressing) stimulus had significant activity in modulation (and particularly downregulation) of in inflammatory markers and processes. As such, these exosomes are contemplated particularly suitable for treatment of various inflammatory conditions and for treatment of pain associated with an inflammatory condition as already discussed above.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the cells or exosomes are administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. Exosomes from tumor cells that were previously exposed to one or more inflammatory stimulus for the treatment of an inflammatory condition and/or pain in a human in need thereof, wherein the exosomes are obtained by stimulating tumor cells with a lipopolysaccharide (LPS); wherein the exosomes express increased miRNA-21 compared to unmodified exosomes that are not stimulated by LPS; wherein the exosomes are formulated for administration via in a syringe or catheter; and wherein administration of the exosomes to the human reduces inflammatory markers and/or alleviates pain in the human.

2. The exosomes of claim 1, wherein the exosomes have an average particle size of between about 70 nm to about 130 nm.

3. The exosomes of claim 1, wherein the exosomes are from the tumor cells of the same human.

4. The exosomes of claim 1, wherein the inflammatory stimulus is selected from the group consisting of IFNy (interferon gamma), TNFa (tumor necrosis factor alpha), a TLR ligand, a NOD ligand, and a STING (Stimulator of Interferon Genes) activator.

5. The exosomes of claim 1, wherein the tumor cells are exposed to the inflammatory stimulus in an amount that increases expression of IDO (indoleamine-2,3-dioxygenase) or PGE2 (prostaglandin E2) in the tumor cells.

6. The exosomes of claim 1, wherein the tumor cells are exposed to the inflammatory stimulus in an amount that increases IL-6, IL-8, IL 10, or CCL-2 in the tumor cells.

7. The exosomes of claim 1, wherein the exosomes are formulated for injection.

* * * * *